(12) United States Patent
Bader et al.

(10) Patent No.: US 9,517,245 B2
(45) Date of Patent: Dec. 13, 2016

(54) SORAFENIB-MICRORNA COMBINATION THERAPY FOR LIVER CANCER

(71) Applicant: Mirna Therapeutics, Inc., Austin, TX (US)

(72) Inventors: Andreas Bader, Austin, TX (US); Jane Zhao, Austin, TX (US)

(73) Assignee: MIRNA THERAPEUTICS, INC., Austin, TX (US)

( * ) Notice: Subject to any disclaimer, the term of this patent is extended or adjusted under 35 U.S.C. 154(b) by 0 days.

(21) Appl. No.: 14/634,243

(22) Filed: Feb. 27, 2015

(65) Prior Publication Data

US 2015/0246070 A1    Sep. 3, 2015

Related U.S. Application Data

(60) Provisional application No. 61/946,110, filed on Feb. 28, 2014.

(51) Int. Cl.
*A61P 35/00* (2006.01)
*A61K 31/713* (2006.01)
*A61K 31/44* (2006.01)
*C12N 15/113* (2010.01)

(52) U.S. Cl.
CPC .............. *A61K 31/713* (2013.01); *A61K 31/44* (2013.01); *C12N 15/113* (2013.01); *C12N 2320/31* (2013.01)

(58) Field of Classification Search
USPC ........ 435/6.11, 6.13, 6.14, 91.1, 91.31, 455; 514/1, 2, 44; 536/23.1, 24.1, 24.5
See application file for complete search history.

(56) References Cited

FOREIGN PATENT DOCUMENTS

WO    2008/154333 A2    12/2008
WO    2011/088309 A1    7/2011

OTHER PUBLICATIONS

Leung et al. "Complete Pathological Remission is Possible with Systemic Combination Chemotherapy for Inoperable Hepatocellular Carcinoma", Clin Cancer Res, vol. 5, Jul. 1999 pp. 1676-1681.
Llovet et al. "Systematic Review of Randomized Trials for Unresectable Hepatocellular Carcinoma: Chemoembolization Improves Survival", Hepatology, Feb. 2003 pp. 429-442.
Zhu et al. "Phase II Study of Gemcitabine and Oxaliplatin in Combination With Bevacizumab in Patients With Advanced Hepatocellular Carcinoma", J of Clinical Oncology, vol. 24, No. 12, Apr. 20, 2006 pp. 1898-1903.
Abou-Alfa et al. "Phase II Study of Sorafenib in Patients With Advanced Hepatocellular Carcinoma", J of Clinical Oncology, vol. 24, No. 26, Sep. 10, 2006 pp. 4293-4300.
Kemeny et al. "Phase I Trial of Systemic Oxaliplatin Combination Chemotherapy With Heptic Arterial Infusion in Patients With Unresectable Liver Metastases From Colorectal Cancer", J of Clinical Oncology, vol. 23, No. 22, Aug. 1, 2005 pp. 4888-4896.
Leung et al. "Factors Predicting Response and Survival in 149 Patients with Unresectable Hepatocellular Carcinoma Treated by Combination Cisplatin, Interferon-alpha, Doxorubicin and 5-Fluorouracil Chemotherapy", Cancer, vol. 94, No. 2, Jan. 15, 2002 pp. 421-427.
Farmer et al. "Current Treatment Modalities for Hepatocellular Carcinoma", Annals of Surgery, vol. 219, No. 3, Mar. 1994 pp. 236-247.
Louafi et al. "Gemcitabine Plus Oxaliplatin (GEMOX) in Patients With Advanced Hepatocellular Carcinoma (HCC)—Results of a Phase II Study", Cancer, vol. 109, No. 7, Apr. 1, 2007 pp. 1384-1390.
Pastorelli et al. "Gemcitabine and liposomal doxorubicin in biliary and hepatic carcinoma (HCC) chemotherapy: preliminary results and review of the literature", Annals of Oncology, vol. 17, supp. 5, 2006 pp. v153-v157.
Marin et al. "Chemotherapy in the treatment of primary liver tumours", Cancer Therapy, vol. 6, 2008 pp. 711-728.
Nishikawa et al. "Hepatic Arterial Infusion Chemotherapy for Advanced Hepatocellular Carcinoma in Japan", Cancers, vol. 4, 2012 pp. 165-183.
Jelic et al. "Hepatocellular carcinoma: ESMO Clinical Practice Guidelines for diagnosis, treatment and follow-up", Annals of Oncology, vol. 21, supp. 5, May 2010 pp. v59-v64.
A. X. Zhu "Systemic Therapy of Advanced Hepatocellular Carcinoma: How Hopeful Should We Be?", The Oncologist, vol. 11, 2006 pp. 790-800.
R. K. Kelley "Brivanib and FOLFOX in Hepatocellular Carcinoma: Finding the Common Themes Among Negative Trials", J of Clinical Oncology, vol. 31, No. 28, Oct. 1, 2013 pp. 3483-3486.
Yang et al. "MicroRNA-34a Targets Bcl-2 and Sensitizes Human Hepatocellular Carcinoma Cells to Sorafenib Treatment", Tech in Cancer Research and Treatment, vol. 13, No. 1, Feb. 2014 pp. 77-86.
Zhu et al. "Biomarkers for hepatocellular carcinoma: progression in early diagnosis, prognosis, and personalized therapy", Biomarker Research, vol. 1, No. 10, 2013 pp. 1-8.
Wako Diagnostics "Hepatocellular Carcinoma Risk Assessment Biomarkers At a Glance", 2013 (2 pages).
Behne et al. "Biomarkers for Hepatocellular Carcinoma", Int J of Hepatology, vol. 2012, 2012 pp. 1-7.
Georges et al. "Coordinated Regulation of Cell Cycle Transcripts by p53-Inducible microRNAs, miR-192 and miR-215", Cancer Res, vol. 68, No. 24, Dec. 15, 2008 pp. 10105-10112.
Zhao et al. "TP53-independent Function of miR-34a via HDAC1 and p21CIP1/WAF1", Mol Ther, vol. 21, No. 9, Sep. 2013 pp. 1678-1686.
Full Prescribing Information for NEXAVAR, 2013 pp. 1-30.
Full Prescribing Information for MEKINST, 2014 pp. 1-38.
Full Prescribing Information for GAZYVA, 2013 pp. 1-15.
Full Prescribing Information for KADCYLA, pp. 1-21.
Full Prescribing Information for PERJETA, 2013 (24 pages).
Full Prescribing Information for AVASTIN, 2013 (26 pages).
Full Prescribing Information for ABRAXANE, 2005-2013, pp. 1-24.

*Primary Examiner* — Jane Zara
(74) *Attorney, Agent, or Firm* — Wilson Sonsini Goodrich & Rosati

(57) ABSTRACT

A method of treating a subject having liver cancer can include administering a synthetic oligonucleotide to a subject having liver cancer, the oligonucleotide comprising a sequence that is at least 80% identical to at least one of SEQ ID NO:1-12 (e.g., a miR-34 or miR-215 mimic); and administering sorafenib to the subject, wherein the molar ratio of sorafenib:oligonucleotide administered to the subject is in the range of about 10-2000 (e.g., a ratio that provides a superior, for example synergistic or greater than additive, effect).

19 Claims, 8 Drawing Sheets

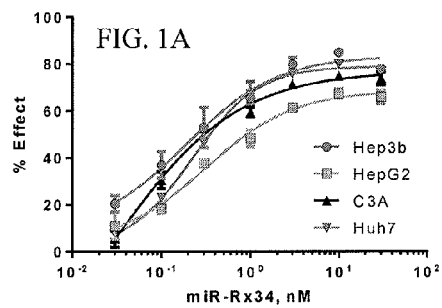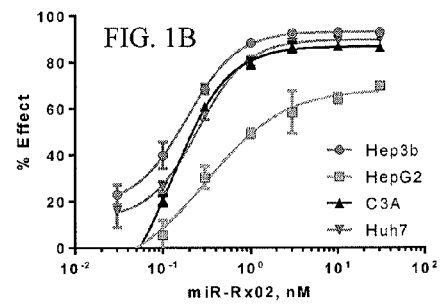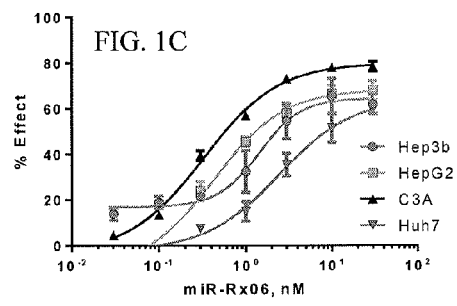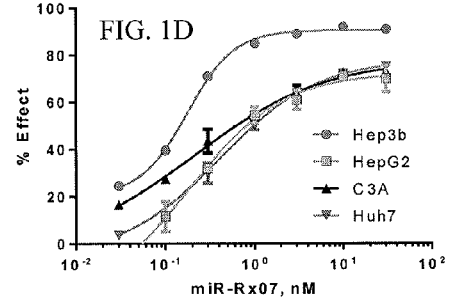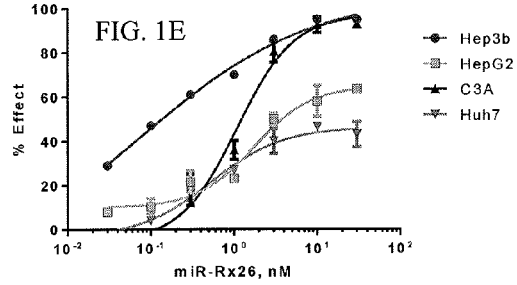

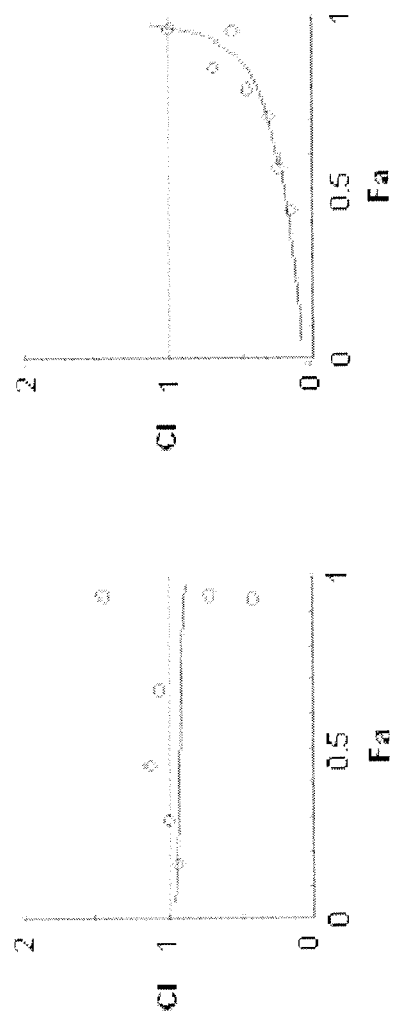
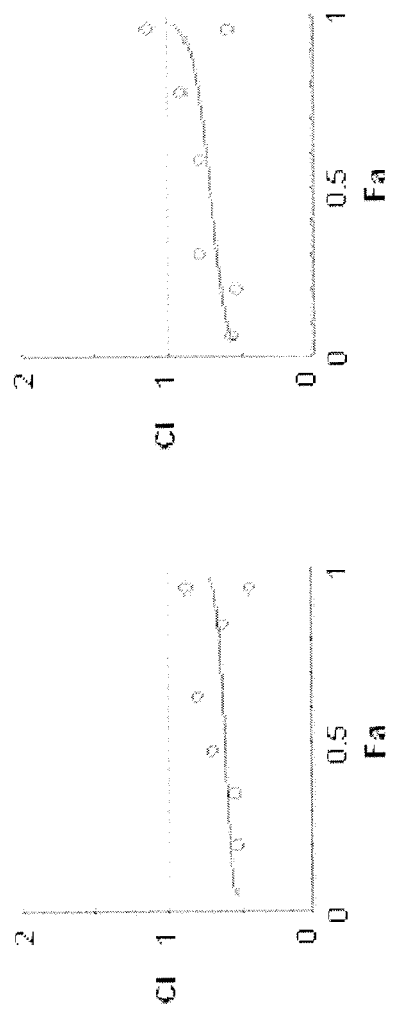
FIG. 3D

SEQUENCE LISTING

```
<160> NUMBER OF SEQ ID NOS: 15

<210> SEQ ID NO 1
<211> LENGTH: 23
<212> TYPE: RNA
<213> ORGANISM: Homo sapiens

<400> SEQUENCE: 1
uggcaguguc uuagcugguu guu                                          23

<210> SEQ ID NO 2
<211> LENGTH: 23
<212> TYPE: RNA
<213> ORGANISM: Homo sapiens

<400> SEQUENCE: 2
uaggcagugu cauuagcuga uug                                          23

<210> SEQ ID NO 3
<211> LENGTH: 23
<212> TYPE: RNA
<213> ORGANISM: Homo sapiens

<400> SEQUENCE: 3
aggcagugua guuagcugau ugc                                          23

<210> SEQ ID NO 4
<211> LENGTH: 22
<212> TYPE: RNA
<213> ORGANISM: Homo sapiens
<220> FEATURE:
<221> NAME/KEY: misc_feature
<222> LOCATION: (1)..(1)
<223> OTHER INFORMATION: n denotes a deletion or any nucleotide(s)
<220> FEATURE:
<221> NAME/KEY: misc_feature
```

```
<222> LOCATION: (10)..(10)
<223> OTHER INFORMATION: n denotes a deletion or any nucleotide(s)
<220> FEATURE:
<221> NAME/KEY: misc_feature
<222> LOCATION: (18)..(18)
<223> OTHER INFORMATION: n denotes a deletion or any nucleotide(s)
<220> FEATURE:
<221> NAME/KEY: misc_feature
<222> LOCATION: (22)..(22)
<223> OTHER INFORMATION: n denotes a deletion or any nucleotide(s)

<400> SEQUENCE: 4
nggcagugun uuagcugnuu gn                                              22

<210> SEQ ID NO 5
<211> LENGTH: 22
<212> TYPE: RNA
<213> ORGANISM: Homo sapiens

<400> SEQUENCE: 5
uggcagugua uuguuagcug gu                                              22

<210> SEQ ID NO 6
<211> LENGTH: 22
<212> TYPE: RNA
<213> ORGANISM: Homo sapiens

<400> SEQUENCE: 6
aggcagugua uuguuagcug gc                                              22

<210> SEQ ID NO 7
<211> LENGTH: 25
<212> TYPE: RNA
<213> ORGANISM: Homo sapiens

<400> SEQUENCE: 7
uaggcagugu auugcuagcg gcugu                                           25

<210> SEQ ID NO 8
<211> LENGTH: 22
<212> TYPE: RNA
<213> ORGANISM: Homo sapiens
<220> FEATURE:
<221> NAME/KEY: misc_feature
<222> LOCATION: (14)..(14)
<223> OTHER INFORMATION: n denotes a deletion or any nucleotide(s)
<220> FEATURE:
<221> NAME/KEY: misc_feature
<222> LOCATION: (19)..(19)
<223> OTHER INFORMATION: n denotes a deletion or any nucleotide(s)
<220> FEATURE:
<221> NAME/KEY: misc_feature
<222> LOCATION: (21)..(21)
<223> OTHER INFORMATION: n denotes a deletion or any nucleotide(s)

<400> SEQUENCE: 8
uggcagugua uugnuagcng ng                                              22

<210> SEQ ID NO 9
<211> LENGTH: 7
<212> TYPE: RNA
<213> ORGANISM: Homo sapiens

<400> SEQUENCE: 9 ggcagug                                                                7

<210> SEQ ID NO 10
```

```
<211> LENGTH: 21
<212> TYPE: RNA
<213> ORGANISM: Homo sapiens

<400> SEQUENCE: 10
cugaccuaug aauugacagc c                                              21

<210> SEQ ID NO 11
<211> LENGTH: 21
<212> TYPE: RNA
<213> ORGANISM: Homo sapiens

<400> SEQUENCE: 11
augaccuaug aauugacaga c                                              21

<210> SEQ ID NO 12
<211> LENGTH: 7
<212> TYPE: RNA
<213> ORGANISM: Homo sapiens

<400> SEQUENCE: 12 ugaccua                                                               7

<210> SEQ ID NO 13
<211> LENGTH: 22
<212> TYPE: RNA
<213> ORGANISM: Homo sapiens

<400> SEQUENCE: 13
uucaaguaau ccaggauagg cu                                             22

<210> SEQ ID NO 14
<211> LENGTH: 21
<212> TYPE: RNA
<213> ORGANISM: Homo sapiens

<400> SEQUENCE: 14
uacaguacug ugauaacuga a                                              21

<210> SEQ ID NO 15
<211> LENGTH: 22
<212> TYPE: RNA
<213> ORGANISM: Homo sapiens

<400> SEQUENCE: 15
uuaaggcacg cggugaaugc ca                                             22
```

SORAFENIB-MICRORNA COMBINATION THERAPY FOR LIVER CANCER

CROSS REFERENCE TO RELATED APPLICATION

This application claims the benefit of U.S. Provisional Application No. 61/946,110, filed Feb. 28, 2014, the disclosure of which is herein incorporated by reference in its entirety.

SEQUENCE LISTING

The instant application contains a Sequence Listing which has been submitted electronically in ASCII format and is hereby incorporated by reference in its entirety. Said ASCII copy, created on Feb. 27, 2015, is named 112172_250_SL.txt and is 3,163 bytes in size.

FIELD OF THE INVENTION

The invention relates to combination therapy (or polytherapy) for cancer, and more specifically, to sorafenib-oligonucleotide (e.g., microRNA mimic) combination therapy for liver cancer.

BACKGROUND OF THE INVENTION

Liver cancer (or hepatic cancer) is a cancer that originates in the liver. Primary liver cancer is the fifth most frequently diagnosed cancer globally and the second leading cause of cancer death. Liver cancers are malignant tumors that grow on the surface or inside the liver. They are formed from either the liver itself or from structures within the liver, including blood vessels or the bile duct.

The leading cause of liver cancer is viral infection with hepatitis B virus or hepatitis C virus. The cancer usually forms secondary to cirrhosis caused by these viruses. For this reason, the highest rates of liver cancer occur where these viruses are endemic, including East-Asia and sub-Saharan Africa. Liver cancers should not be confused with liver metastases, also known as secondary liver cancer, which is a cancer that originate from organs elsewhere in the body and migrate to the liver.

The most frequent liver cancer, accounting for approximately 75% of all primary liver cancers, is hepatocellular carcinoma (HCC). HCC is a cancer formed by liver cells, known as hepatocytes that become malignant. Another type of cancer formed by liver cells is hepatoblastoma, which is specifically formed by immature liver cells. It is a rare malignant tumor that primarily develops in children, and accounts for approximately 1% of all cancers in children and 79% of all primary liver cancers under the age of 15.

Liver cancer can also form from other structures within the liver such as the bile duct, blood vessels and immune cells. Cancer of the bile duct (cholangiocarcinoma and cholangiocellular cystadenocarcinoma) account for approximately 6% of primary liver cancers. There is also a variant type of HCC that consists of both HCC and cholangiocarcinoma. Tumors of the liver blood vessels include angiosarcoma and hemangioendothelioma. Embryonal sarcoma and fibrosarcoma are produced from a type of connective tissue known as mesenchyme. Cancers produced from muscle in the liver are leiomyosarcoma and rhabdomyosarcoma. Other less common liver cancers include carcinosarcomas, teratomas, yolk sac tumors, carcinoid tumors and lymphomas. Lymphomas usually have diffuse infiltration to liver, but it may also form a liver mass in rare occasions.

Surgical resection is often the treatment of choice for non-cirrhotic livers. Increased risk of complications such as liver failure can occur with resection of cirrhotic livers. 5-year survival rates after resection has massively improved over the last few decades and can now exceed 50%. Recurrence rates after resection due to the spread of the initial tumor or formation of new tumors exceeds 70%. Liver transplantation can also be used in cases of HCC where this form of treatment can be tolerated and the tumor fits specific criteria (e.g., the Milan criteria). Less than 30-40% of individuals with HCC are eligible for surgery and transplant because the cancer is often detected late stage. Also, HCC can progress during the waiting time for liver transplants, which can ultimately prevent a transplant.

Percutaneous ablation is the only non-surgical treatment that can offer cure. There are many forms of percutaneous ablation, which consist of either injecting chemicals into the liver (ethanol or acetic acid) or producing extremes of temperature using radio frequency ablation, microwaves, lasers or cryotherapy. Of these, radio frequency ablation has one of the best reputations in HCC, but the limitations include inability to treat tumors close to other organs and blood vessels due to heat generation and the heat sync effect, respectively.

Systemic chemotherapeutics are not routinely used in HCC, although local chemotherapy may be used in a procedure known as transarterial chemoembolization. In this procedure, cytotoxic drugs such as doxorubicin or cisplatin with lipiodol are administered and the arteries supplying the liver are blocked by gelatin sponge or other particles. Because most systemic drugs have no efficacy in the treatment of HCC, research into the molecular pathways involved in the production of liver cancer produced Sorafenib, a targeted therapy drug that prevents cell proliferation and blood cell growth in some circumstances.

Radiotherapy is not often used in HCC because the liver is not tolerant to radiation. Although with modern technology it is possible to provide well targeted radiation to the tumor, minimizing the dose to the rest of the tumor. Dual treatments of radiotherapy plus chemoembolization, local chemotherapy, systemic chemotherapy or targeted therapy drugs may show benefit over radiotherapy alone.

Sorafenib (marketed as NEXAVAR®), is a FDA-approved drug for patients with advanced primary liver cancer. It is a small molecule interacting with multiple intracellular and cell surface kinases and unique in targeting the Raf/Mek/Erk pathway. By inhibiting these kinases, genetic transcription involving cell proliferation and angiogenesis is inhibited. However, even with the development of drugs like sorafenib, the current treatment options for liver cancer are insufficient due to its limited effectiveness and severe toxicity.

Research into new therapeutics and improving existing therapeutics is ongoing, but has not yielded any clinically relevant breakthroughs. In one example, researchers hypothesized that microRNA technology might improve known therapeutics such as sorafenib. See Yang et al. "MicroRNA-34a Targets Bcl-2 and Sensitizes Human Hepatocellular Carcinoma Cells to Sorafenib Treatment" 1-10 Technology in Cancer Research and Treatment 2013 Jul. 11. However, the work was limited in that it did not establish synergy, or a greater than additive effect, between microRNA and sorafenib and it did not establish any clinically relevant information or guidance on dosing. The nature of drug-drug interactions and whether the two agents cooperate synergistically, additively of antagonistically can vary depending on drug ratios, drug concentrations and the desired potency. Therefore, drug combinations are typically evaluated using a mathematical algorithm based on Loewe's model of additivity. In this model, combination index (CI) values are calculated that are derived from dose-response curves of the single agents alone when used alone and in combination. CI<1, CI=1, and CI>1 indicate synergistic, additive and antagonistic interactions, respectively.

Thus, new therapies are needed to improve patient outcome and reduce toxicity.

SUMMARY OF THE INVENTION

The invention is based, at least in part, on the discovery that certain combinations of sorafenib and microRNA are particularly effective at inhibiting, and preventing the proliferation of, liver cancer cells. This discovery can be described as a synergy, or greater than additive effect, that is specific to sorafenib, miR-34 and miR-215, and liver cancer (e.g., HCC). This discovery is consistent for miR-34 and miR-215 across multiple liver cancer cell types, but does not necessarily extend directly to other microRNAs, chemotherapeutic agents, and/or cancers. Furthermore, this discovery does not extend to all ratios sorafenib and miR-34 or miR-215—some ratios are approximately additive and others are antagonistic. Accordingly, the invention provides methods and compositions for treating liver cancer, including liver cancer cells and liver cancer cells in a subject, whereby sorafenib and a miR-34 or miR-215 mimic are administered in a ratio that is particularly effective (e.g., synergistic or more than additive).

For example, in various aspects and embodiments, the invention includes a method of treating a subject having liver cancer (or a subject having primary liver cancer, or a subject having HCC). The method includes administering a synthetic oligonucleotide to the subject. The oligonucleotide includes a sequence that is at least 80% identical to at least one of SEQ ID NO:1-12. The method also includes administering sorafenib to the subject. The molar ratio of sorafenib:oligonucleotide (i.e., the molar ratio of the sorafenib and oligonucleotide administered to the subject) is about 10-2000 (i.e., in the range of about 10-2000).

In various aspects and embodiments, the invention includes a method of inhibiting proliferation of liver cancer cells (or primary liver cancer cells, or HCC cells). The method includes administering a synthetic oligonucleotide to the cells. The oligonucleotide includes a sequence that is at least 80% identical to at least one of SEQ ID NO:1-12. The method also includes administering sorafenib to the cells. The molar ratio of sorafenib:oligonucleotide is about 10-2000.

In various aspects and embodiments, the invention includes a method of inhibiting proliferation of liver cancer cells. The method includes administering an oligonucleotide to liver cancer cells, the oligonucleotide comprising a sequence that is at least 80% identical to at least one of SEQ ID NO:1-12; and administering sorafenib to the cells, wherein the molar ratio of sorafenib:oligonucleotide is about 10-2000.

In various aspects and embodiments, the invention includes a method of treating a subject having hepatocellular carcinoma (HCC). The method includes administering an oligonucleotide to a subject having HCC, the oligonucleotide comprising a sequence that is at least 80% identical to at least one of SEQ ID NO:1-12; and administering sorafenib to the subject, wherein the molar ratio of sorafenib:oligonucleotide is about 10-2000 and has a combination index (CI)<1.

In various aspects and embodiments, the invention includes a method of treating a subject having hepatocellular carcinoma (HCC). The method includes administering about 10, 20, 25, 30, 40, 50, 75, 100, 125, 150, 175, 200, 225, or 250 mg/m$^2$ per day of an oligonucleotide to a subject having HCC, the oligonucleotide comprising a sequence that is at least 80% identical to at least one of SEQ ID NO:1-12; and administering about 800, 600, 400, or 200 mg/day of sorafenib to the subject, wherein the molar ratio of sorafenib:oligonucleotide is about 10-2000 based on the amount of sorafenib:oligonucleotide administered to the subject in a single day, a single week, 14 days, 21 days, or 28 days, and wherein the molar ratio of sorafenib:oligonucleotide has a combination index (CI) of less than about 0.95, 0.90, 0.85, 0.80, 0.75, 0.70, 0.65, 0.60, 0.55, 0.50, 0.45, 0.40, 0.35, 0.30, 0.25, or 0.20.

In various embodiments, any of the aspects and embodiments can be combined with any one or more of the features below. For example:

In some embodiments, the liver cancer is primary liver cancer.

In some embodiments, the liver cancer is hepatocellular carcinoma (HCC).

In some embodiments, the sequence is at least 80% identical to at least one of SEQ ID NO:1-4.

In some embodiments, the sequence is at least 80% identical to SEQ ID NO:1.

In some embodiments, the sequence is at least 85, 90, 95, or 100% identical.

In some embodiments, the molar ratio exhibits synergy.

In some embodiments, the synergy is quantified as a combination index (CI) of less than about 0.80, 0.75, 0.70, 0.65, 0.60, 0.55, 0.50, 0.45, 0.40, 0.35, 0.30, 0.25, or 0.20.

In some embodiments, the molar ratio is in the range of about 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, or 250-300.

In some embodiments, the molar ratio is in the range of about 15-1723, 15-492, 60-197, 30-492, 52-1723, or about 30, 40, 53, 60, 70, 79, 89, 98, 106, 141, 197, 266, 311, or 931.

In some embodiments, the molar ratio is based on the amount of sorafenib:oligonucleotide administered to the subject in a single day, a single week, 14 days, 21 days, or 28 days.

In some embodiments, the oligonucleotide is administered to the subject in: 1, 2, 3, 4, 5, 6, or 7 daily doses over 7 days; 1, 2, 3, 4, 5, 6, 7, 8, 9, 10, 11, 12, 13, or 14 daily doses over 14 days; 1, 2, 3, 4, 5, 6, 7, 8, 9, 10, 11, 12, 13, 14, 15, 16, 17, 18, 19, 20, or 21 daily doses over 21 days; or 1, 2, 3, 4, 5, 6, 7, 8, 9, 10, 11, 12, 13, 14, 15, 16, 17, 18, 19, 20, 21, 22, 23, 24, 25, 26, 27, or 28 daily doses over 28 days.

In some embodiments, the oligonucleotide is administered to the subject for: 2 weeks (total 14 days); 1 week with 1 week off (total 14 days); 3 consecutive weeks (total 21 days); 2 weeks with 1 week off (total 21 days); 1 week with 2 weeks off (total 21 days); 4 consecutive weeks (total 28 days); 3 consecutive weeks with 1 week off (total 28 days); 2 weeks with 2 weeks off (total 28 days); or 1 week with 3 consecutive weeks off (total 28 days).

In some embodiments, the oligonucleotide is administered: on day 1 of a 7, 14, 21 or 28 day cycle; on days 1 and 15 of a 21 or 28 day cycle; on days 1, 8, and 15 of a 21 or 28 day cycle; or on days 1, 2, 8, and 15 of a 21 or 28 day cycle.

The method of claim 1, wherein the oligonucleotide is administered once every 1, 2, 3, 4, 5, 6, 7, or 8 weeks.

In some embodiments, the oligonucleotide is administered for 1, 2, 3, 4, 5, 6, 7, 8, 9, 10, 11, or 12 cycles.

In some embodiments, the oligonucleotide is administered prior to the sorafenib, concurrently with the sorafenib, or after the sorafenib.

In some embodiments, the dose of sorafenib is about 800, 600, 400, or 200 mg/day.

In some embodiments, the dose of oligonucleotide is about 10, 20, 25, 30, 40, 50, 75, 100, 125, 150, 175, 200, 225, or 250 mg/m$^2$ per day.

In some embodiments, the liver cancer has primary or secondary resistance to sorafenib.

In some embodiments, the oligonucleotide is between 17 and 30 nucleotides in length and comprises (i) a microRNA region having a sequence from 5' to 3' that is at least 80% identical to SEQ ID NO:1 or SEQ ID NO:11, and (ii) a complementary region having a sequence from 5' to 3' that is 60-100% complementary to the microRNA region.

In some embodiments, the oligonucleotide is between 17 and 30 nucleotides in length and comprises one or more of the following (i) a replacement group for phosphate or hydroxyl of the nucleotide at the 5' terminus of the complementary strand of the molecule; (ii) one or more sugar modifications in the first or last 1 to 6 residues of the complementary region; or (iii) noncomplementarity between one or more nucleotides in the last 1 to 5 residues at the 3' end of the complementary region and the corresponding nucleotides of the microRNA region.

In some embodiments, the oligonucleotide is between 17 and 30 nucleotides in length and comprises (i) at least one modified nucleotide that blocks the 5' OH or phosphate at the 5' terminus, wherein the at least one nucleotide modification is an NH$_2$, biotin, an amine group, a lower alkylamine group, an acetyl group or 2'oxygen-methyl (2'O-Me) modification; or (ii) at least one ribose modification selected from 2'F, 2'NH$_2$, 2'N$_3$, 4'thio, or 2'O—CH$_3$.

In some embodiments, the oligonucleotide is between 17 and 30 nucleotides in length and comprises (i) a first polynucleotide having a sequence with at least 80% sequence identity to SEQ ID NO:1 or SEQ ID NO:11; (ii) a separate second polynucleotide having a sequence from 5' to 3' that is 60-100% complementary to the first polynucleotide; and (iii) a lower alkylamine group at the 5' end of the complementary strand.

In some embodiments, the liver cancer is hepatocellular carcinoma (HCC); the sequence is at least 80% identical to SEQ ID NO:1 or SEQ ID NO:11; and the molar ratio has a combination index (CI)<1.

In some embodiments, the sequence is at least 80% identical to at least one of SEQ ID NO:5-8.

In some embodiments, the sequence is at least 80% identical to SEQ ID NO:9.

In some embodiments, the sequence is at least 80% identical to SEQ ID NO:10.

In some embodiments, the sequence is at least 80% identical to SEQ ID NO:11.

In some embodiments, the sequence is at least 80% identical to SEQ ID NO:12.

In some embodiments, the oligonucleotide is 7-130, 7-30, 7-25, 15-30, 15-25, 17-30, 17-25, 7, 8, 9, 10, 12, 13, 14, 15, 16, 17, 18, 19, 20, 21, 22, 23, 24, 25, 26, 27, 28, 29, or 30 nucleobases long.

In some embodiments, the oligonucleotide has a double stranded or hairpin structure.

In some embodiments, the oligonucleotide is not administered by transfection.

In some embodiments, the subject is not a cell culture or tissue culture.

In some embodiments, the subject is a human, mouse, rat, guinea pig, rabbit, pig, or non-human primate.

Various other aspects, embodiments, and features of the invention are described in detail below and presented in the claims. That being said, the foregoing and following descriptions are illustrative and explanatory only and are not restrictive of the invention, as claimed.

BRIEF DESCRIPTION OF THE FIGURES

FIG. 1A-D illustrates dose-effect curves of miRNA mimics in liver cancer cells. Serially diluted miRNAs (0.03-30 nM) were reverse transfected in liver cancer cells, and cell proliferation or percent inhibition (effect) were determined by AlamarBlue 6 days post transfection. Data were normalized to mock-transfected cells. FIG. 1A present data for miR-34, FIG. 1B present data for miR-124a, FIG. 1C present data for miR-215, FIG. 1D present data for miR-101, and FIG. 1E present data for miR-26a.

FIG. 3A-D illustrates combination index (CI) plots showing actual CI values vs. the level of cancer cell inhibition on an axis from 0 (no inhibition) to 1 (100% inhibition). Combinations that are considered synergistic and have clinical value are those with a low CI value (<0.6) at maximal cancer cell inhibition. FIG. 3A present data for miR-34, FIG. 3B present data for miR-101, FIG. 3C present data for miR-26a, and FIG. 3D present data for miR-215.

DETAILED DESCRIPTION OF THE INVENTION

Figure 2:
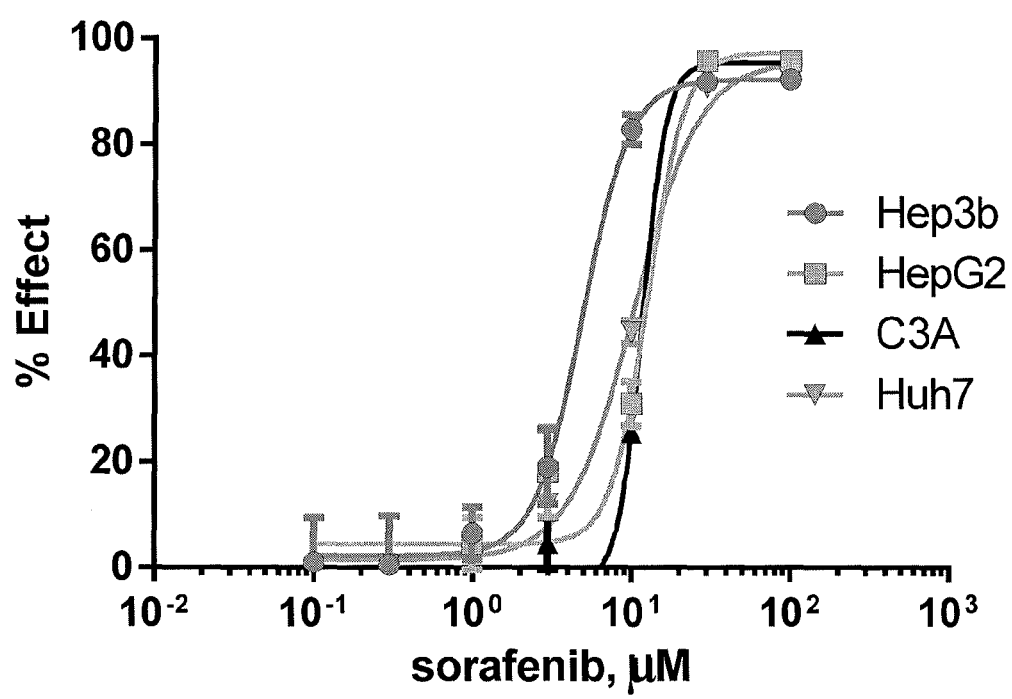
FIG. 2 illustrates dose-effect curves of sorafenib in liver cancer cells. Cells were seed in 96-well plate at 2000 cells per well. Three days after seeding the cells, sorafenib in a serial dilution from (0.1-100 µM) was added to the medium. Cell proliferation or percent inhibition was determined by AlamarBlue 3 days post drug treatment. Data were normalized to cells treated with sorafenib solvent (1% DMSO final concentration).

The invention is based, at least in part, on the discovery that certain combinations of sorafenib and microRNA are particularly effective at inhibiting, and preventing the proliferation of, liver cancer cells. This discovery can be described as a synergy, or greater than additive effect, that is specific to certain combinations of sorafenib and miR-34 and miR-215, and liver cancer. This discovery is consistent for specific concentrations of miR-34 and miR-215 across multiple liver cancer cell types, but does not necessarily extend directly to other microRNAs, chemotherapeutic agents, and/or cancers. Indeed, most drugs do not synergize and many can antagonize. Even where synergy is present, it may exist only within a certain range of concentrations. Accordingly, the invention provides unexpectedly advantageous methods and compositions for treating liver cancer, including liver cancer cells and liver cancer cells in a subject, whereby sorafenib and a miR-34 or miR-215 mimic are administered in a ratio that is particularly effective (e.g., synergistic or more than additive).

MicroRNAs and Synthetic Oligonucleotides

MicroRNAs (miRNAs) are small non-coding, naturally occurring RNA molecules that post-transcriptionally modulate gene expression and determine cell fate by regulating multiple gene products and cellular pathways (Bartel, Cell, 2004. 116(2):281-97). miRNAs interfere with gene expression by either degrading the mRNA transcript by blocking the protein translation machinery (Bartel, supra). miRNAs target mRNAs with sequences that are fully or partially complementary which endows these regulatory RNAs with the ability to target a broad but nevertheless specific set of mRNAs. To date, there are ~1,500 human annotated miRNA genes with roles in processes as diverse as cell proliferation, differentiation, apoptosis, stem cell development, and immune function (Costinean et al., Proc Natl Acad Sci USA, 2006. 103(18):7024-9). Often, the misregulation of miRNAs can contribute to the development of human disease including cancer (Esquela-Kerscher et al., Nat Rev Cancer, 2006. 6(4):259-69; Calin et al., 2006. 6(11):857-66). miRNAs deregulated in cancer can function as bona fide tumor suppressors or oncogenes. A single miRNA can target multiple oncogenes and oncogenic signaling pathways (Forgacs et al., Pathol Oncol Res, 2001. 7(1):6-13), and translating this ability into a future therapeutic may hold the promise of creating a remedy that is effective against tumor heterogeneity. Thus, miRNAs have the potential of becoming powerful therapeutic agents for cancer (Volinia et al., Proc Natl Acad Sci USA, 2006. 103(7):2257-61; Tong et al., Cancer Gene Ther, 2008. 15(6):341-55) that act in accordance with our current understanding of cancer as a "pathway disease" that can only be successfully treated when intervening with multiple cancer pathways (Wiggins et al., Cancer Res, 2010. 70(14): 5923-5930; Jones et al., Science, 2008. 321(5897): 1801-6; Parsons et al., Science, 2008. 321(5897):1807-12).

As of March 2013, Mirna Therapeutics (Austin, Tex.) has completed the preclinical development program to support the manufacture of cGMP-materials and the conduction of IND-enabling studies for a miR-34-based supplementation therapy (miR-34-Mim). Mirna evaluated the toxicity as well as the pharmacokinetic profile of the formulation containing miR-34 mimic in non-GLP pilot studies using mice, rats and non-human primates. These experiments did not show adverse events at the predicted therapeutic levels of miR-34-Mim, as measured by clinical observations, body weights, clinical chemistries (including LFT, RFT and others), hematology, gross pathology, histopathology of select organs and complement ($CH_{50}$). In addition, miRNA mimics formulated in lipid nanoparticles do not induce the innate immune system as demonstrated in fully immunocompetent mice, rats, non-human primates, as well as human whole blood specimens. A more detailed review of the pre-clinical data is provided in Bader, Front Genet. 2012; 3:120.

In methods of the inventions, a specific synthetic oligonucleotide (e.g., synthetic microRNA mimic) is administered to a subject as part of a combination therapy with sorafenib. In specific embodiments, the oligonucleotide is a mimic of miR-34a, miR-34b, miR-34c, miR-449a, miR-449b, miR-449c, miR-192, or miR-215. These microRNAs are well known in the art, and one of skill in the art would understand that they include the conventional naturally occurring sequences and any chemically modified versions and sequence homologues thereof. Representative sequences are provided in Table 1 below.

In various aspects and embodiments, the present invention employs a synthetic oligonucleotide as a microRNA mimic—as such, the oligonucleotide or microRNA is not transfected into a subject cell. Rather, in various embodiments, the oligonucleotide is administered by injection or transfusion. Rather than an isolated cell, tissue, or culture thereof, the subject can be a mammal (e.g., a human or laboratory animal such as a mouse, rat, guinea pig, rabbit, pig, non-human primate, and the like). Similarly, the present invention does not use antisense, RNA interference (RNAi), or analogous technologies. Again, this is an important distinction because the oligonucleotides or microRNAs of the invention are "sense" strands or mimics, which is the polar opposite of antisense and RNAi.

In general, the oligonucleotides used in connection with the invention are 7-130 nucleotides long, double stranded RNA molecules, either having two separate strands or a hairpin structure. For example, an oligonucleotide can be 7, 8, 9, 10, 12, 13, 14, 15, 16, 17, 18, 19, 20, 21, 22, 23, 24, 25, 26, 27, 28, 29, 30, 7-30, 7-25, 15-30, 15-25, 17-30, or 17-25 nucleotides long. One of the two strands, which is referred to as the "guide strand", contains a sequence which is identical or substantially identical to the seed sequence (nucleotide positions 2-9) of the parent microRNA sequence shown in the table below. "Substantially identical", as used herein, means that at most 1 or 2 substitutions and/or deletions are allowed. In some embodiments, the guide strand comprises a sequence which is at least 80%, 85%, 90%, 95% identical to the respective full length sequence provided herein. The second of the two strands, which is referred to as a "passenger strand", contains a sequence that is complementary or substantially complementary to the seed sequence of the corresponding given microRNA. "Substantially complementary", as used herein, means that at most 1 or 2 mismatches and/or deletions are allowed. In some embodiments, the passenger strand comprises a sequence which is at least 60%, 65%, 70%, 75%, 80%, 85%, 90%, 95% identical to the complement of the respective full length sequence provided herein. In some embodiments, the oligonucleotide is a mimic of miR-34a, miR-34b, miR-34c, miR-449a, miR-449b, miR-449c, miR-192, or miR-215, or an analog or homolog thereof. In some embodiments, the oligonucleotide includes the seed sequence of one of these microRNAs.

TABLE 1 microRNA Sequences and Sequence Identification Numbers

| microRNA | Sequence | SEQ ID NO: |
|---|---|---|
| miR-34a | UGGCAGUGUCUUAGCUGGUUGUU | SEQ ID NO: 1 |
| miR-34b | UAGGCAGUGUCAUUAGCUGAUUG | SEQ ID NO: 2 |
| miR-34c | AGGCAGUGUAGUUAGCUGAUUGC | SEQ ID NO: 3 |
| miR-34 consensus | *GGCAGUGU*UUAGCUG*UUG* | SEQ ID NO: 4 |
| miR-449a | UGGCAGUGUAUUGUUAGCUGGU | SEQ ID NO: 5 |
| miR-449b | AGGCAGUGUAUUGUUAGCUGGC | SEQ ID NO: 6 |
| miR-449c | UAGGCAGUGUAUUGCUAGCGGCUGUS | SEQ ID NO: 7 |
| miR-449 consensus | UGGCAGUGUAUUG*UAGC*G*G | SEQ ID NO: 8 |
| miR-34/449 seed | GGCAGUG | SEQ ID NO: 9 |

TABLE 1-continued microRNA Sequences and
Sequence Identification Numbers

| microRNA | Sequence | SEQ ID NO: |
|---|---|---|
| miR-192 | CUGACCUAUGAAUUGACAGCC | SEQ ID NO: 10 |
| miR-215 | AUGACCUAUGAAUUGACAGAC | SEQ ID NO: 11 |
| miR-192/215 seed | UGACCUA | SEQ ID NO: 12 |
| miR-26a | UUCAAGUAAUCCAGGAUAGGCU | SEQ ID NO: 13 |
| miR-101 | UACAGUACUGUGAUAACUGAA | SEQ ID NO: 14 |
| miR-124a | UUAAGGCACGCGGUGAAUGCCA | SEQ ID NO: 15 |

"*" denotes a deletion or any nucleotide(s).
The miR-34/449 and miR-192/215 seed sequences are shown in bold highlighting.

Synthetic oligonucleotides can be formulated in liposomes such as, for example, those described in U.S. Pat. Nos. 7,858,117 and 7,371,404; US Patent App. Pub. Nos. 2009-0306194 and 2011-0009641. Other delivery technologies are available, including lipid or various ligand conjugates, etc.

Synthetic oligonucleotides can also be chemically modified, for example, synthetic oligonucleotides can have a 5' cap on the passenger strand (e.g., $NH_2$—$(CH_2)_6$—O—) and/or a mismatch at the first and/second nucleotide of the same strand. Other possible chemical modifications can include backbone modifications (e.g., phosphorothioate, morpholinos), ribose modifications (e.g., 2'-OMe, 2'-Me, 2'-F, 2'-4'-locked/bridged sugars (e.g., LNA, ENA, UNA) as well as nucleobase modifications (see, e.g., Peacock et al, 2011. J Am Chem Soc., 133(24):9200-9203. In certain embodiments, the synthetic oligonucleotides have modifications as described in U.S. Pat. No. 7,960,359 and US Patent Application Pub. Nos. 2012-0276627 and 2012-0288933.

In some embodiments, the synthetic oligonucleotide is between 17 and 30 nucleotides in length and comprises (i) a microRNA region having a sequence from 5' to 3' that is at least 80% identical to at least one of SEQ ID NO:1-12, and (ii) a complementary region having a sequence from 5' to 3' that is 60-100% complementary to the microRNA region.

In some embodiments, the synthetic oligonucleotide comprises a sequence that is at least 80, 85, 90, 95, or 100% identical to at least one of SEQ ID NO:1-12.

In some embodiments, the synthetic oligonucleotide comprises a single polynucleotide or a double stranded polynucleotide. In some embodiments, the synthetic oligonucleotide comprises a hairpin polynucleotide.

In some embodiments, the synthetic oligonucleotide is between 17 and 30 nucleotides in length and comprises (i) a first polynucleotide having a sequence with at least 80% identical to at least one of SEQ ID NO:1-12; and (ii) a separate second polynucleotide having a sequence from 5' to 3' that is 60-100% complementary to the first polynucleotide.

In some embodiments, the synthetic oligonucleotide is between 17 and 30 nucleotides in length and comprises one or more of the following (i) a replacement group for phosphate or hydroxyl of the nucleotide at the 5' terminus of the complementary strand of the RNA molecule; (ii) one or more sugar modifications in the first or last 1 to 6 residues of the complementary region; or (iii) noncomplementarity between one or more nucleotides in the last 1 to 5 residues at the 3' end of the complementary region and the corresponding nucleotides of the microRNA region.

In some embodiments, the synthetic oligonucleotide is between 17 and 30 nucleotides in length and comprises (i) at least one modified nucleotide that blocks the 5' OH or phosphate at the 5' terminus, wherein the at least one nucleotide modification is an NH2, biotin, an amine group, a lower alkylamine group, an acetyl group or 2'oxygen-methyl (2'O-Me) modification; or (ii) at least one ribose modification selected from 2'F, 2'NH$_2$, 2'N$_3$, 4'thio, or 2'O—CH$_3$.

In some embodiments, the synthetic oligonucleotide is between 17 and 30 nucleotides in length and comprises (i) a first polynucleotide having a sequence with at least 80% identical to at least one of SEQ ID NO:1-12; (ii) a separate second polynucleotide having a sequence from 5' to 3' that is 60-100% complementary to the first polynucleotide; and (iii) a lower alkylamine group at the 5' end of the complementary strand.

In some embodiments, the synthetic oligonucleotide is between 17 and 30 nucleotides in length and comprises (i) a first polynucleotide having 100% identical to at least one of SEQ ID NO:1-12; (ii) a separate second polynucleotide having a sequence from 5' to 3' that is 100% complementary to the first polynucleotide; and (iii) a lower alkylamine group at the 5' end of the complementary strand.

Synthetic oligonucleotides can generally be administered intravenously as a slow-bolus injection at doses ranging 0.001-6.0 mg/kg per dose, for example, 0.01-3.0, 0.025-1.0 or 0.25-0.5 mg/kg per dose, with one, two, three or more doses per week for 2, 4, 6, 8 weeks or longer as necessary. Further description and details on synthetic oligonucleotide dosing and administration are provided in the Combination Chemotherapy section below.

Sorafenib

The invention, in various aspects and embodiments, includes the use of sorafenib (i.e., sorafenib tosylate as well as other pharmaceutically acceptable forms, salts, and esters of sorafenib). Sorafenib is commercially available as NEXAVAR®, which is the tosylate salt of sorafenib. Sorafenib tosylate has the chemical name 4-(4-{3-[4-Chloro-3 (trifluoromethyl)phenyl]ureido} phenoxy) N-methylpyridine-2-carboxamide 4-methylbenzenesulfonate and its structural formula is:

Formula I

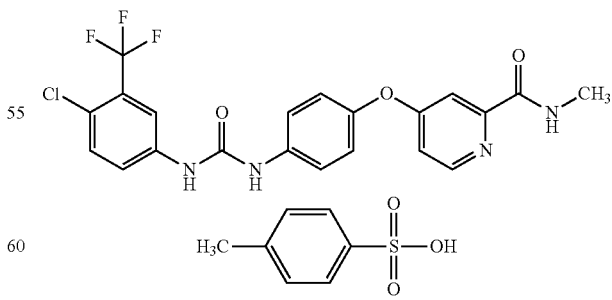

Sorafenib tosylate is a white to yellowish or brownish solid with a molecular formula of $C_{21}H_{16}ClF_3N_4O_3 \times C_7H_8O_3S$ and a molecular weight of 637.0 g/mol. Sorafenib tosylate is practically insoluble in aqueous media, slightly soluble in ethanol and soluble in PEG 400. Sorafenib is also described in U.S. Pat. Nos. 7,235,576, 7,235,576, 7,897,623, and 8,124,630.

Dosage and administration of sorafenib is approved for 400 mg (2 tablets) orally twice daily without food. However, treatment interruption and/or dose reduction may be needed to manage suspected adverse drug reactions. In such cases, dose may be reduced to 400 mg once daily or to 400 mg every other day (see, e.g., the FDA label for NEXAVAR® tablets, oral, Initial U.S. Approval: 2005). A person of ordinary skill will understand that sorafenib dosage and administration can follow medically approved guidelines, as well medically accepted deviations or alterations to such guidelines. Further description and details on sorafenib dosing and administration are provided in the Combination Chemotherapy section below.

Liver Cancer

The invention, in various aspects and embodiments, is applicable to the treatment of liver cancer cells, including cancer cells in a subject or in vitro treatment of isolated cancer cells. If the cancer cells are in a subject, the subject can be a primate, such as a human, with liver cancer. The subject can be a mammal, such a mammal other than a mouse. The subject can be an adult human (i.e., 18 years or older), or a juvenile human (i.e., less than 18 years old).

In various embodiments, the liver cancer (e.g., HCC) is not resistant to sorafenib. Alternatively, the liver cancer (e.g., HCC) can have primary or secondary resistance to sorafenib. The subject can be a responder to sorafenib in the absence of the microRNA or synthetic oligonucleotide. The subject can be a non-responder to sorafenib in the absence of the microRNA or synthetic oligonucleotide. In some embodiments, the subject has undergone a prior treatment with sorafenib lasting at least 2, 4, 6, 8, 10 months or longer. In other embodiments, the subjects are patients who have experienced one or more significant adverse side effect to sorafenib and therefore require a reduction in dose.

In various embodiments, the liver cancer (e.g., HCC) is intermediate, advanced, or terminal stage. The liver cancer (e.g., HCC) can be metastatic or non-metastatic. The liver cancer (e.g., HCC) can be resectable or unresectable. The liver cancer (e.g., HCC) can comprise a single tumor, multiple tumors, or a poorly defined tumor with an infiltrative growth pattern (into portal veins or hepatic veins). The liver cancer (e.g., HCC) can comprise a fibrolamellar, pseudoglandular (adenoid), pleomorphic (giant cell), or clear cell pattern. The liver cancer (e.g., HCC) can comprise a well differentiated form, and tumor cells resemble hepatocytes, form trabeculae, cords, and nests, and/or contain bile pigment in cytoplasm. The liver cancer (e.g., HCC) can comprise a poorly differentiated form, and malignant epithelial cells are discohesive, pleomorphic, anaplastic, and/or giant. In some embodiments, the liver cancer (e.g., HCC) is associated with hepatits B, hepatitis C, cirhhosis, or type 2 diabetes.

In some embodiments, the subject is a human having an Eastern Cooperative Oncology Group (ECOG) performance status ≤2.

In some embodiments, the subject is a human having acceptable liver function defined as (i) total bilirubin ≤1.5 times the upper limit of normal (ULN); for patients with hepatocellular carcinoma only, total bilirubin ≤3 mg/dL (i.e., Child-Pugh Score for bilirubin is no greater than 2); (ii) aspartate aminotransferase (AST), alanine aminotransferase (ALT) and alkaline phosphatase (ALP) ≤5×ULN; or (iii) acceptable renal function: • Serum creatinine ≤1.5 times the ULN, or calculated creatinine clearance ≥60 mL/min/1.73 $m^2$ for patients with creatinine levels above 1.5 times the institutional normal.

In some embodiments, the subject is a human having acceptable hematological status defined as (i) absolute Neutrophil Count (ANC) ≥1500 cells/$mm^3$; (ii) platelet count ≥100,000 plts/$mm^3$ (without transfusion); ≥75,000 pits/$mm^3$ for patients with hepatocellular carcinoma only; or (iii) hemoglobin ≥9 g/dL.

In some embodiments, the subject is a human having a prothrombin time (PT) or International Normalized Ratio (INR) ≤1.25×ULN; INR <1.7 or prothrombin time (PT) or <4 seconds above ULN (i.e., Child-Pugh Score is no greater than 1 for the coagulation parameter); or serum albumin >2.8 g/dL (i.e., Child-Pugh Score for albumin is no greater than 2).

In some embodiments, the subject is a human having a prothrombin Child-Pugh Class A (score 5-6) disease. Score for hepatic encephalopathy must be 1; the score for ascites must be no greater than 2 and clinically irrelevant; for the determination of the Child-Pugh Class.

In some embodiments, the subject is a human that does not have a New York Heart Association (NYHA) Class III or IV cardiac disease, myocardial infarction within the past 6 months, unstable and/or symptomatic arrhythmia, or evidence of ischemia on ECG.

In some embodiments, the subject does not have an active, uncontrolled bacterial, viral, or fungal infections requiring systemic therapy.

In some embodiments, the subject is a human that is not a pregnant or nursing woman.

In some embodiments, the subject is a human that does not have a known infection with human immunodeficiency virus (HIV).

In some embodiments, the subject is a human that does not have a serious nonmalignant disease (e.g., hydronephrosis, liver failure, or other conditions) that could compromise the therapy.

In some embodiments, the subject is a human that does not have a recent history of hemorrhage and patients predisposed to hemorrhage due to coagulopathies or structural anomalies.

In some embodiments, the subject is a human that does not require treatment with therapeutic doses of coumarin-type anticoagulants.

In some embodiments, the subject is a human that does not have a cirrhosis classed as Child-Pugh B or C.

In some embodiments, the subject is a human that wherein the subject has an alpha-fetoprotein (AFP) >10, 50, 100, 200, 300, 400, or 500 ng/mL.

In some embodiments, the subject is a human that wherein the subject has an elevates (>10%) AFP-L3 level.

In some embodiments, the subject is a human that has a Des-Gamma-Carboxy (Abnormal) Prothrombin (DCP) >5, 7.5, 10, 25, 50, 75, or 100 ng/mL.

In some embodiments, the subject is a human that has an abnormal level of an epidermal growth factor receptor (EGFR) (erbB-1), c-erb-2 (Her-2/neu), c-erb-3 (HER-3), c-erb-4 (HER-4), or a combination thereof.

In some embodiments, the subject is a human that has an abnormal level of Alpha-Fetoprotein (AFP); Glypican-3 (GPC3); Des-Gamma-Carboxy (Abnormal) Prothrombin (DCP); Serum gamma-glutamyl transferase (GGT); Alpha-1-fucosidase (AFU); Human Carbonyl Reductase 2; Golgi phosphoprotein 2 (GOLPH2); Transforming Growth Factor-Beta (TGF-Beta); Tumor-Specific Growth Factor (TSGF); Hepatocyte growth factor/scatter factor (HGF/SF); Basic Fibroblast Growth Factor; Alpha-Fetoprotein mRNA (AFP mRNA); Gamma-Glutamyl Transferase mRNA (GGT mRNA); Insulin-Like Growth Factor II (IGF-II) mRNA; Albumin mRNA; DKK1; Golgi protein 73 (GP73); Protein induced by vitamin K absence or antagonist II (PIVKA-II); miR-122, miR-192, miR-21, miR-223, miR-26a, miR-27a, and miR-801, or a combination thereof.

Combination Chemotherapy

Combination chemotherapy or polytherapy is the use of more than one medication or other therapy (e.g., as opposed to monotherapy, which is any therapy taken alone). As used herein with reference to the present invention, the term refers to using specific combinations (e.g., ratios and/or dosing schedules) of sorafenib and an oligonucleotide (e.g., miR-34 or miR-215 mimic).

More particularly, the invention provides methods and compositions for treating liver cancer where the sorafenib and oligonucleotide (e.g., miR-34 or miR-215 mimic) are administered in a ratio that is particularly effective (e.g., synergistic or more than additive). In various embodiments, the ratio (e.g., molar ratio of sorafenib:oligonucleotide) is about 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, or 250-300. In some embodiments, the molar ratio is, or is at least, about 50, 100, 150, 200, 250, 300, 350, 400, 450, 500, 550, 600, 650, 700, 750, 800, 850, 900, 950, or 1000. In some embodiments, the molar ratio is, or is less than, about 1000, 1050, 1100, 1150, 1200, 1250, 1300, 1350, 1400, 1450, 1500, 1550, 1600, 1650, 1700, 1750, 1800, 1850, 1900, 1950, or 2000. Examples of molar ratios are about 15-1723, 15-492, 60-197, 30-492, 52-1723, 30, 40, 53, 60, 70, 79, 89, 98, 106, 141, 197, 266, 311, or 931. Other examples are provided throughout the specification and examples.

As used herein for describing ranges, e.g., of ratios, doses, times, and the like, the terms "about" embraces variations that are within the relevant margin of error, essentially the same (e.g., within an art-accepted confidence interval such as 95% for phenomena that follow a normal or Gaussian distribution), or otherwise does not materially change the effect of the thing being quantified.

The molar ratio of sorafenib:oligonucleotide can be measured over different periods of time. For example, the molar ratio can be the amount of sorafenib:oligonucleotide administered to the subject in a single day, a single week, 14 days, 21 days, or 28 days.

The sorafenib dosing amount and/or schedule can follow clinically approved, or experimental, guidelines. In various embodiments, the dose of sorafenib is about 800, 600, 400, or 200 mg/day. A 200 mg/day dose can be administered as a 400 mg dose ever other day.

Likewise the oligonucleotide dosing amount and/or schedule can follow clinically approved, or experimental, guidelines. In various embodiments, the dose of oligonucleotide is about 10, 20, 25, 30, 40, 50, 75, 100, 125, 150, 175, 200, 225, or 250 mg/m$^2$ per day. The dose can be set, within a therapeutically effective range, based upon a selected ratio and dose of sorafenib. As discussed above, the ratio can be determined using the amount of oligonucleotide administered to a subject over a single day, a single week, 14 days, 21 days, or 28 days.

In various embodiments the oligonucleotide is administered to the subject in 1, 2, 3, 4, 5, 6, or 7 daily doses over a single week (7 days). The oligonucleotide can be administered to the subject in 1, 2, 3, 4, 5, 6, 7, 8, 9, 10, 11, 12, 13, or 14 daily doses over 14 days. The oligonucleotide can be administered to the subject in 1, 2, 3, 4, 5, 6, 7, 8, 9, 10, 11, 12, 13, 14, 15, 16, 17, 18, 19, 20, or 21 daily doses over 21 days. The oligonucleotide can be administered to the subject in 1, 2, 3, 4, 5, 6, 7, 8, 9, 10, 11, 12, 13, 14, 15, 16, 17, 18, 19, 20, 21, 22, 23, 24, 25, 26, 27, or 28 daily doses over 28 days.

In various embodiments the oligonucleotide is administered for: 2 weeks (total 14 days); 1 week with 1 week off (total 14 days); 3 consecutive weeks (total 21 days); 2 weeks with 1 week off (total 21 days); 1 week with 2 weeks off (total 21 days); 4 consecutive weeks (total 28 days); 3 consecutive weeks with 1 week off (total 28 days); 2 weeks with 2 weeks off (total 28 days); 1 week with 3 consecutive weeks off (total 28 days).

In various embodiments the oligonucleotide is: administered on day 1 of a 7, 14, 21 or 28 day cycle; administered on days 1 and 15 of a 21 or 28 day cycle; administered on days 1, 8, and 15 of a 21 or 28 day cycle; or administered on days 1, 2, 8, and 15 of a 21 or 28 day cycle. The oligonucleotide can be administered once every 1, 2, 3, 4, 5, 6, 7, or 8 weeks.

A course of sorafenib-oligonucleotide (e.g., miR-34 or miR-215 mimic) therapy can be prescribed by a clinician. The oligonucleotide (and hence the combination therapy) can be administered for 1, 2, 3, 4, 5, 6, 7, 8, 9, 10, 11, or 12 cycles.

A course of sorafenib-oligonucleotide (e.g., miR-34 or miR-215 mimic) therapy can be continued until a clinical endpoint is met. In some embodiments, the therapy is continued until disease progression or unacceptable toxicity occurs. In some embodiments, the therapy is continued until achieving a pathological complete response (pCR) rate defined as the absence of liver cancer (e.g., HCC). In some embodiments, the therapy is continued until partial or complete remission of the liver cancer. Administering the oligonucleotide and the sorafenib to a plurality of subject having HCC increases the Overall Survival (OS), the Progression free Survival (PFS), the Disease Free Survival (DFS), the Response Rate (RR), the Quality of Life (QoL), or a combination thereof.

In various embodiments, the treatment reduces the size and/or number of the liver cancer tumor(s). The treatment can prevent the liver cancer tumor(s) from increasing in size and/or number. The treatment can prevent the liver cancer tumor(s) from metastasizing.

In the methods of the invention, administration is not limited to any particular delivery system and may include, without limitation, parenteral (including subcutaneous, intravenous, intramedullary, intraarticular, intramuscular, or intraperitoneal injection), rectal, topical, transdermal, or oral (for example, in capsules, suspensions, or tablets). Administration to an individual may occur in a single dose or in repeat administrations, and in any of a variety of physiologically acceptable salt forms, and/or with an acceptable pharmaceutical carrier and/or additive as part of a pharmaceutical composition. Physiologically acceptable salt forms and standard pharmaceutical formulation techniques, dosages, and excipients are well known to persons skilled in the art (see, e.g., Physicians' Desk Reference (PDR®) 2005, 59th ed., Medical Economics Company, 2004; and Remington: The Science and Practice of Pharmacy, eds. Gennado et al. 21th ed., Lippincott, Williams & Wilkins, 2005).

Additionally, effective dosages achieved in one animal may be extrapolated for use in another animal, including humans, using conversion factors known in the art. See, e.g., Freireich et al., Cancer Chemother Reports 50(4):219-244 (1966) and Table 2 for equivalent surface area dosage factors).

TABLE 2 equivalent surface area dosage factors

| | From: | | | | |
|---|---|---|---|---|---|
| To: | Mouse (20 g) | Rat (150 g) | Monkey (3.5 kg) | Dog (8 kg) | Human (60 kg) |
| Mouse | 1 | 0.5 | 0.25 | 0.17 | 0.08 |
| Rat | 2 | 1 | 0.5 | 0.25 | 0.14 |
| Monkey | 4 | 2 | 1 | 0.6 | 0.33 |
| Dog | 6 | 4 | 1.7 | 1 | 0.5 |
| Human | 12 | 7 | 3 | 2 | 1 |

The combination therapies of the invention are not specifically limited to any particular course or regimen and may be employed separately or in conjunction with other therapeutic modalities (e.g., chemotherapy or radiotherapy).

In various embodiments, the oligonucleotide is administered prior to the sorafenib, concurrently with the sorafenib, after the sorafenib, or a combination thereof. The oligonucleotide can be administered intravenously. The oligonucleotide can be administered systemically or regionally.

A combination therapy in accordance with the present invention can include additional therapies (e.g., pharmaceutical, radiation, and the like) beyond the sorafenib and oligonucleotide. Similarly, the present invention can be used as an adjuvant therapy (e.g., when combined with surgery). In various embodiments, the subject is also treated by surgical resection, percutaneous ethanol or acetic acid injection, transcatheter arterial chemoembolization, radiofrequency ablation, laser ablation, cryoablation, focused external beam radiation stereotactic radiotherapy, selective internal radiation therapy, intra-arterial iodine-131-lipiodol administration, and/or high intensity focused ultrasound.

The combination of the oligonucleotide and sorafenib can be used as an adjuvant, neoadjuvant, concomitant, concurrent, or palliative therapy. The combination of the oligonucleotide and sorafenib can be used as a first line therapy, second line therapy, or crossover therapy.

In some embodiments, the therapeutically effective dose of sorafenib is reduced through combination with the oligonucleotide. For example, the weekly or monthly dose of sorafenib can be reduced by at least 10%, 20%, 30%, 40%, 50%, 60%, 70%, 80%, 90% or more relative to the maximum recommended dose or the maximum tolerated dose. In other embodiments, sorafenib is administered at an effective dose that at least 50%, 60%, 70%, 80%, 90% or more below the dose needed to be effective in the absence of the oligonucleotide (or microRNA inhibitor) administration. In some embodiments, the IC50 of sorafenib is reduced by at least 4-, 5-, 10-, 20-, 30-, 40-, 50-, or 100-fold relative to the IC50 in the absence of the synthetic oligonucleotide (or microRNA inhibitor).

Further description and embodiments of combination therapies are provided in the Examples section below.

Synergy and Combination Index (CI) Values

As discussed above, and further illustrated in the examples below, the present invention provides methods and compositions for treating liver cancer where the sorafenib and miR-34 are administered in a ratio that is particularly effective (e.g., synergistic or more than additive). While synergy and synonymous terms are commonly used in the art, the property is not always defined or quantified (and, hence, the purported synergy may not actually be present). In connection with the present invention and the examples below, combination index (CI) values were used to quantify the effects of various combinations of sorafenib and oligonucleotides.

CI values were based on Loewe's additivity model were determined to assess the nature of drug-drug interactions that can be additive (CI=1), antagonistic (CI>1), or synergistic (CI<1) for various drug-drug concentrations and effect levels (Fa, fraction affected; inhibition of cancer cell proliferation). CI values were calculated based on linear regression trendlines using the CompuSyn software (ComboSyn Inc., Paramus, N.J.), following the method by Chou et al., whereby the hyperbolic and sigmoidal dose-effect curves are transformed into a linear form (Chou TC (2010) Drug combination studies and their synergy quantification using the Chou-Talalay method. Cancer Res 70: 440-6, instructions also available at ComboSyn, Inc., www.combosyn.com).

In various embodiments, the molar ratio of sorafenib:oligonucleotide exhibits a CI<1 in liver cancer (e.g., HCC). The molar ratio of sorafenib:oligonucleotide can exhibits a CI<0.95, 0.90, 0.85, 0.80, 0.75, 0.70, 0.65, 0.60, 0.55, 0.50, 0.45, 0.40, 0.35, 0.30, 0.25, or 0.20 in liver cancer (e.g., HCC). In one embodiment, the oligonucleotide is miR-34 (e.g., a miR-34 mimic) and the CI<0.60. CI can be used in conjunction with other parameters, for example CI<0.60, DRI>2, and Fa>65%. In one embodiment, the oligonucleotide is miR-215 (or a miR-215 mimic) and the CI<0.80, 0.75, 0.70, 0.65, 0.60, 0.55, or 0.50 (and optionally in combination with other parameters, for example DRI>2, and Fa>65%).

The following examples provide illustrative embodiments of the invention. One of ordinary skill in the art will recognize the numerous modifications and variations that may be performed without altering the spirit or scope of the present invention. Such modifications and variations are encompassed within the scope of the invention. The Examples do not in any way limit the invention.

EXAMPLES

Example 1

Sorafenib and miRNAs Combination Studies in Liver Cancer Cells

Objective:

Investigate whether therapeutic miRNA mimics cooperate synergistically with sorafenib to inhibit cultured liver cancer cells.

Summary:

miR-34-Mim, miR-124a-Mim, miR-101-Mim, and miR-26a-Mim are mimics of potent therapeutic miRNAs miR-124a, miR-215, miR-101, and miR-26a, respectively. As miR-449 has the same seed sequence as miR-34, miR-34-Mim can also be considered a miR-449 mimic. As miR-192 has the same seed sequence as miR-215, miR-215-Mim can also be considered a miR-192 mimic. Here, we identified miR-34-Mim and miR-215-Mim as miRNA mimics that synergize with sorafenib in four liver cancer cell lines. The data indicate that the synergism between miR-34-Mim and sorafenib was observed at specific combination ratios and at a high level of cancer cell inhibition.

Introduction:

MicroRNAs (miRNAs), a class of small, non-coding RNAs can function as tumor suppressors. miRNAs inhibit multiple oncogenic gene products and pathways and are therefore likely to ameliorate drug resistance and to function synergistically with other anti-cancer agents. This example shows a series of pre-clinical and clinical drug candidates that are subjects for combination studies with sorafenib. The miRNA/sorafenib combinations were tested according to Chou-Talalay's algorithm based on Loewe's additivity model to produce combination index (CI) values that indicate additive (CI=1), synergistic (CI<1) or antagonistic (CI>1) drug effects. Combination effects were determined in four liver cancer cell lines.

Material and Reagents:
miRNAs: miR-34-Mim (Ambion, Cat# AM16099, Lot# ASO0012XE)
    miR-124a-Mim (Ambion, Cat# AM17104, Lot# ASO0L5VC)
    miR-215-Mim (Ambion, Cat# AM17104, Lot# ASO0M54V)
    miR-101-Mim (Ambion, Cat# AM17104, Lot# ASO0M5VA)
    miR-26a-Mim (TriLink, Lot# M109-E01B)

The miRNA manufactures are in-vivo ready quality and prepared as a 600 nM stock solution in nuclease-free $H_2O$
Sorafenib: 10 mM in DMSO (LC Laboratories, CAT# S-8502, Lot# BSF-105)
Cell Lines: Hep3b, HepG2, C3A (ATCC HB-8064, HB-8065, CRL-10741) and Huh7 (Japan)
Cell culture medium: EMEM (ATCC, Cat#30-2003, Lot#60946371)
    DMEM (Gibco, Cat#11320-033, Lot#1147373)
    Trypsin (Gibco, Cat#25300-054)
    PBS (Ambion, Cat# AM9625)
    Opti-MEM (Gibco, Cat#31985-070, Lot#1293625)
Lipofectamine RNAiMAX transfection reagent (Life Technology, Cat#13778-150, Lot#1233863)
Instruments: PolarStar Optima plate reader (BMG Labtech)
Data Analysis: IC50 of sorafenib and miRNAs were determined using the GraphPad (Prism) software. Combination index values (CI) and dose reduction index values (DRI) were determined using the CompuSyn software. DRI reflects the change (e.g., reduction where synergy is present) in drug concentration required to achieve a predetermined effect between (i) the drug in a monotherapy and (ii) the same drug in a combination therapy.

Experimental Procedures miRNA mimics in a serial dilution were reverse transfected into liver cancer cells using LipofectamineRNAiMAX following a protocol described in LAB-SOP-018. Cellular proliferation was determined using AlamarBlue (Invitrogen). Six days post transfection, nonlinear regression curves and IC50 values were calculated using the GraphPad (Prism) software.

Sorafenib dose response curves were established in each cell line, and the cell proliferation was determined using AlamarBlue (Invitrogen) 3 days post drug treatment. Nonlinear regression and IC50 values were calculated using the GraphPad (Prism) software.

Combination studies were carried out such that each miRNA and sorafenib was used at a constant ratio as indicated in the plate layout in Table 3 below. Each data point was done in triplicates.

TABLE 3

| | | | |
|---|---|---|---|
| 8x IC50 | c1 | c1 | c1/c1 |
| 4x IC50 | c2 | c2 | c2/c2 |
| 2x IC50 | c3 | c3 | c3/c3 |
| IC50 | c4 | c4 | c4/c4 |
| 0.5x IC50 | c5 | c5 | c5/c5 |
| 0.25x IC50 | c6 | c6 | c6/c6 |
| 0.125x IC50 | c7 | c7 | c7/c7 |
| 0 | mock | mock | mock |
| | Sorafenib alone | miRNA alone | Sorf/miRNA |

First, miRNAs were reverse transfected at concentrations as indicated in Table 3. Then, 3 days post transfection, the supernatant was replaced with fresh media (90 μL per well), and sorafenib was added at concentrations as shown above in Table 3 (10 μL per well). Cellular proliferation was determined 3 days post sorafenib treatment. CI and DRI values were calculated using CompuSyn software.

For the miR-34-Mim/sorafenib combination, the effects were determined at multiple drug ratios in Hep3B cells using a full plate layout (both fixed concentration and constant ratio methods, see below). Each data point was done in triplicates, and each experiment was independently repeated three times.

TABLE 4

| | | | miR-34-Mim | | | | | | | |
|---|---|---|---|---|---|---|---|---|---|---|
| | | | mock | 8X IC50 C1 | 4X IC50 C2 | 2x IC50 C3 | 1X IC50 C4 | 0.5X IC50 C5 | 0.25X IC50 C6 | 0.125X IC50 C7 |
| sorafenib | 8X IC50 | C1 | | | | | | | | |
| | 4X IC50 | C2 | | | | | | | | |
| | 2x IC50 | C3 | | | | | | | | |
| | 1X IC50 | C4 | | | | | | | | |
| | 0.5X IC50 | C5 | | | | | | | | |
| | 0.25X IC50 | C6 | | | | | | | | |
| | 0.125X IC50 | C7 | | | | | | | | |

All control and standards values were within the limits of the assay.

Results:

Dose response curve and IC50 values of miRNAs and sorafenib in liver cancer cells are shown in FIGS. 1 and 2.

FIG. 1 illustrates dose-effect curves of the tested miRNA mimics in liver cancer cells. As described above, serially diluted miRNAs (0.03-30 nM) were reverse transfected in liver cancer cells, and cell proliferation or percent inhibition (effect) were determined by AlamarBlue 6 days post transfection. IC50 values were calculated using the GraphPad software. FIG. 1A present data for miR-34, FIG. 1B present data for miR-124a, FIG. 1C present data for miR-215, FIG. 1D present data for miR-101, and FIG. 1E present data for miR-26a.

FIG. 2 illustrates dose-effect curves of sorafenib in liver cancer cells. Cells were seed in 96-well plate at 2000 cells per well. Three days after seeding the cells, sorafenib in a serial dilution from (0.1-100 µM) was added to the medium. Cell proliferation or percent inhibition was determined by AlamarBlue 3 days post drug treatment, and IC50 values were calculated using the GraphPad software.

TABLE 5

Figure 3A:
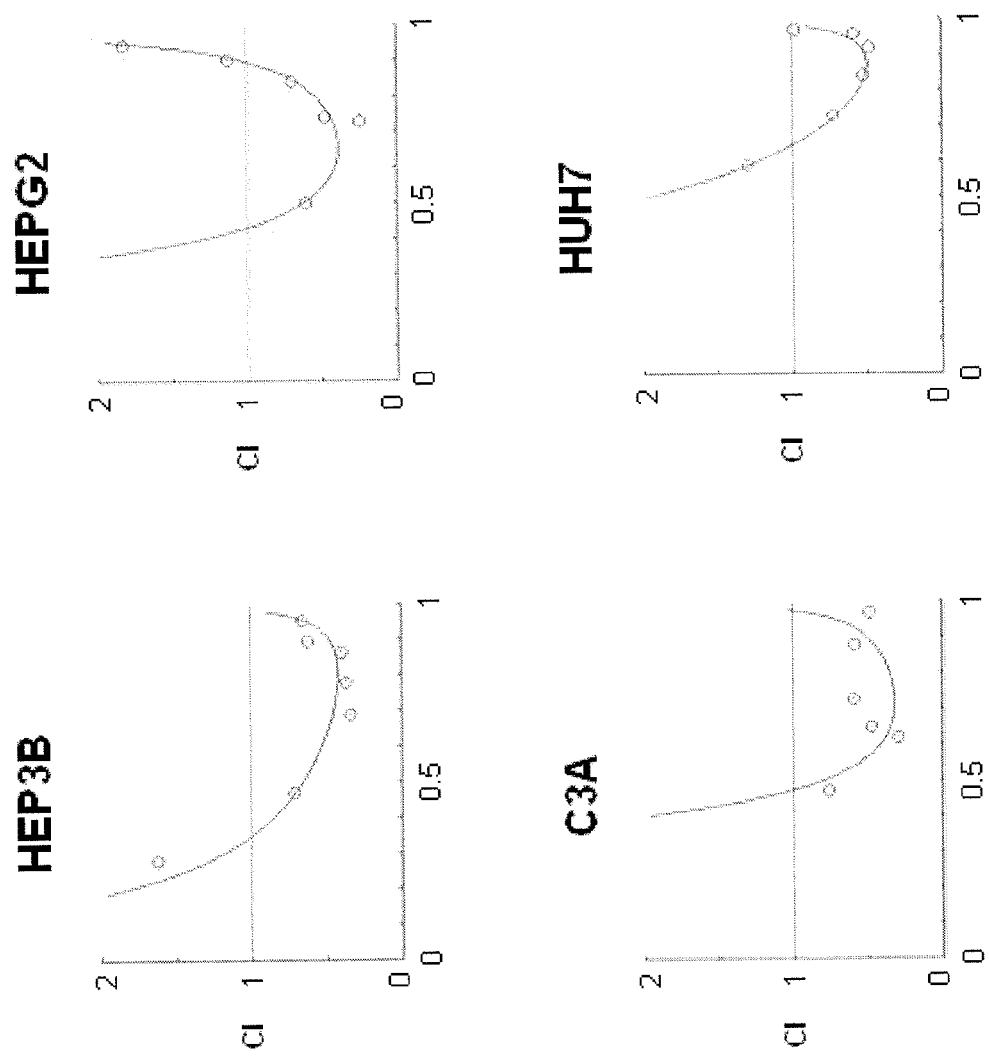
Figure 3B:
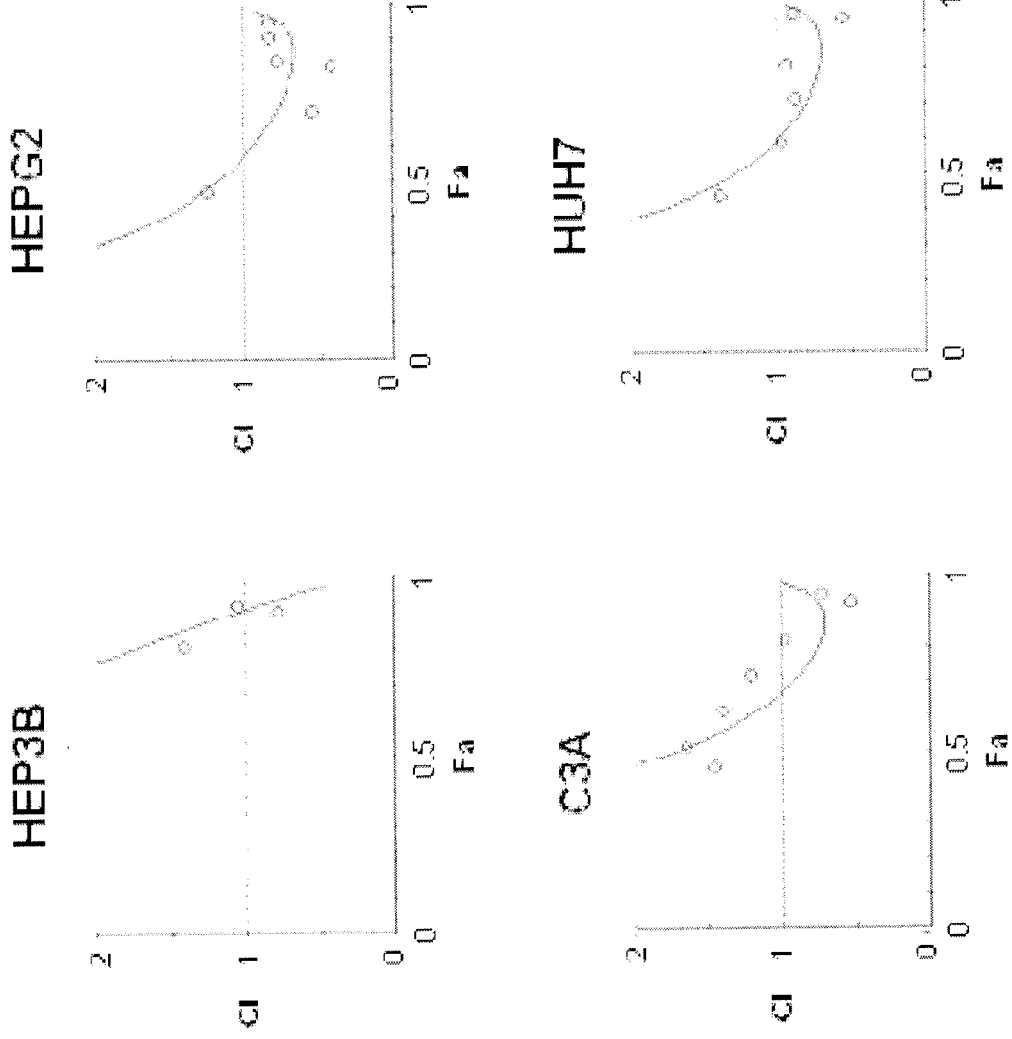
Figure 3C:
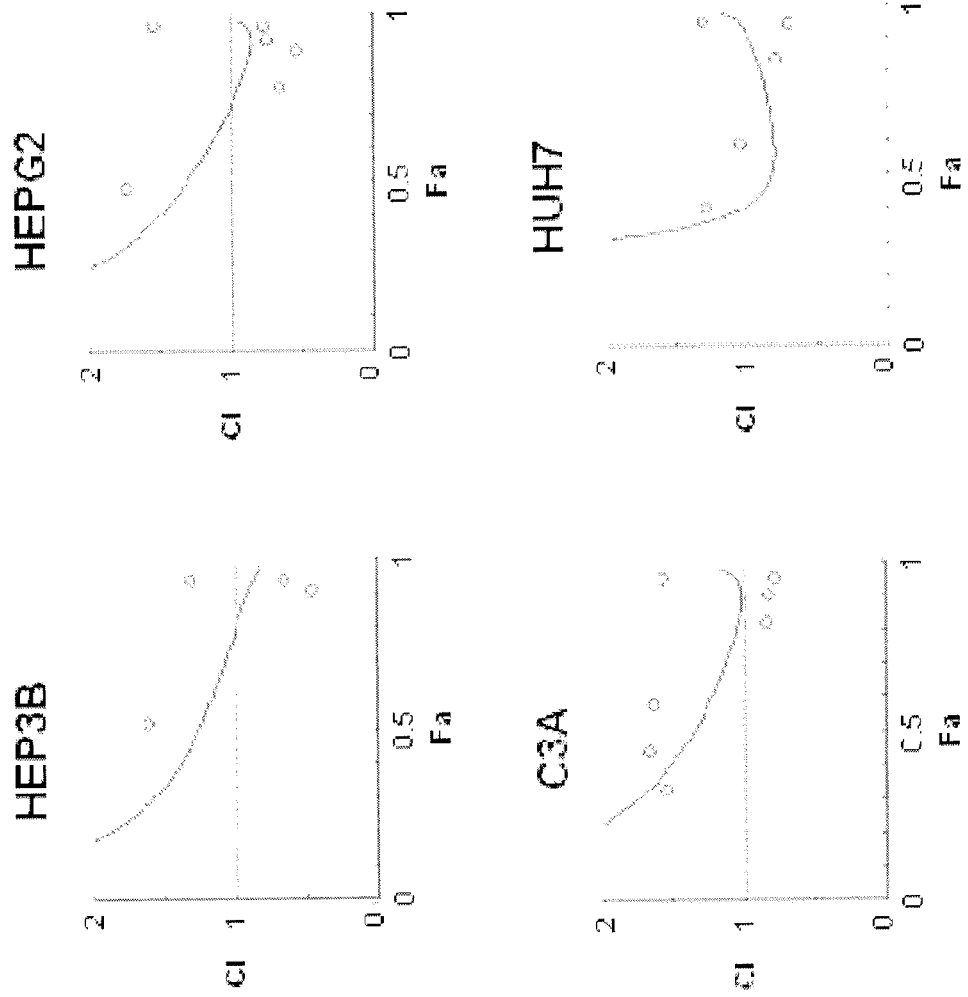

| IC50 | Hep3b | HepG2 | HUH7 | C3A |
|---|---|---|---|---|
| Sorafenib, µM | 5.4-12.7 | 6.7-9.0 | 13.1-16.0 | 10.66-11.8 |
| miR-34-Mim, nM | 0.3-7.2 | 1.7-6 | 0.2-0.61 | 0.25-0.53 |
| miR-124-Mim, nM | 0.09-0.13 | 2.3-7.4 | 0.23-0.24 | 0.17-0.28 |
| miR-215-Mim, nM | 0.76-3.87 | 2.8-11.6 | 3.5-11.35 | 0.3-0.87 |
| miR-101-Mim, nM | 0.07-0.21 | 1.7-11.6 | 1.78-1.48 | 0.33-0.91 |
| miR-26-Mim, nM | 0.14-0.17 | 3.5-5.97 | *n/a | 1.15-1.3 | lines were generated using the Compusyn software. Combinations that are considered synergistic and have clinical value are those with a low CI value (preferably below 0.6) at maximal cancer cell inhibition. As shown above, miR-34-Mim was the sole mimic that synergized with sorafenib consistently across all four HCC cell lines. CI, combination index; Fa, fraction affected (=inhibition of proliferation). Data points below the horizontal line indicate synergy. FIG. 3A present data for miR-34, FIG. 3B present data for miR-101, FIG. 3C present data for miR-26a, and FIG. 3D present data for miR-215.

An accurate evaluation of drug-drug interactions is complex because outcomes depend on drug ratios, drug concentrations and desired potency. Specifically and as shown in FIG. 3, CI values are greater 1 at low drug concentrations and below 1 at higher drug concentrations, indicating antagonistic interactions at low drug concentrations and synergy at higher concentrations.

TABLE 6A

CI and DRI values of the miR-34-Mim/sorafenib combination in four HCC cell lines - single ratio. CI and DRI values at any given effect of miR-34-Mim in combination with sorafenib. Values were determined using CompuSyn software. The upper and lower data indicated two independent experiments.

| | CI Value at Inhibition of | | | | sorafenib DRI Value at Inhibition of | | | | miR-34-Mim DRI Value at Inhibition of | | |
|---|---|---|---|---|---|---|---|---|---|---|---|
| | 50% | 75% | 90% | 95% | 50% | 75% | 90% | 95% | 50% | 75% | 80% |
| Hep3b | 0.68 | 0.47 | 0.52 | 0.68 | 6.5 | 3.8 | 2.2 | 1.6 | 1.9 | 4.8 | 6.2 |
| | 0.39 | 0.33 | 0.59 | 1.1 | 12.7 | 4.8 | 1.8 | 0.96 | 3.2 | 8.2 | 10.5 |
| HepG2 | 0.63 | 0.46 | 1.1 | 2 | 6 | 2.4 | 0.93 | 0.5 | 2.2 | 27.8 | 54.2 |
| | 0.85 | 0.45 | 0.69 | 1.1 | 6.2 | 3 | 1.5 | 0.91 | 1.4 | 8.5 | 13.5 |
| C3A | 0.8 | 0.33 | 0.51 | 0.72 | 5.6 | 3.3 | 1.98 | 1.4 | 1.6 | 33.9 | 75.2 |
| | 1.39 | 0.53 | 0.44 | 0.45 | 4.8 | 3.5 | 2.6 | 2.1 | 0.8 | 4.1 | 6.2 |
| Huh7 | 1.95 | 0.65 | 0.51 | 0.65 | 7.2 | 4.1 | 2.4 | 1.6 | 0.6 | 2.5 | 3.6 |
| | 1.33 | 0.98 | 0.85 | 0.82 | 1.8 | 1.6 | 1.5 | 1.4 | 1.3 | 2.7 | 3.3 |

TABLE 6B

CI and DRI values of the miR-215-Mim/sorafenib combination in four HCC cell lines - single ratio. Values were determined using CompuSyn software.

| | CI Value at Inhibition of | | | | sorafenib DRI Value at Inhibition of | | | | miR-215-Mim DRI Value at Inhibition of | | |
|---|---|---|---|---|---|---|---|---|---|---|---|
| | 50% | 75% | 90% | 95% | 50% | 75% | 90% | 95% | 50% | 75% | 80% |
| Hep3b | 0.92 | 0.91 | 0.89 | 0.88 | 1.1 | 1.1 | 1.1 | 1.1 | 2.5 | 6.3 | 8.0 |
| HepG2 | 0.21 | 0.35 | 0.57 | 0.81 | 4.8 | 2.9 | 1.7 | 1.23 | 0.6 | 2.4 | 3.4 |
| C3A | 0.61 | 0.64 | 0.67 | 0.69 | 1.65 | 1.57 | 1.5 | 1.4 | 1.3 | 2.0 | 2.3 |
| Huh7 | 0.71 | 0.78 | 0.85 | 0.91 | 1.4 | 1.3 | 1.2 | 1.1 | 3.1 | 5.5 | 6.0 |

Table 5 lists IC50 of sorafenib and miRNAs that were determined using GraphPad. The table shows a range of IC50 values derived from two or three experiments. Since miR-26-Mim was not very potent in Huh7 cells, the calculation of IC50 was not possible, and the combination was not tested in this cell line.

FIG. 3 illustrates combination index (CI) plots of miRNA/sorafenib combinations—single ratio. The CI plots showing actual CI values vs. the level of cancer cell inhibition on an axis from 0 (no inhibition) to 1 (100% inhibition). Trend- CI and DRI values of the miR-34-Mim/sorafenib combination in Hep3B cells—multiple ratios are listed in Tables 7-10 below.

The synergism between sorafenib and miR-34-Mim was observed at multiple combination ratios in Hep3B cells. The highlighted area indicates synergism that meets the following criteria: level of cancer cell inhibition >70%; CI<0.6; DRI>2.

TABLE 7

% Cancer cell inhibition

| sorf, μM | miR-34-Mim | | | | | | | |
|---|---|---|---|---|---|---|---|---|
| | 0 | 0.44 nM | 0.875 nM | 1.75 nM | 3.5 nM | 7 nM | 14 nM | 28 nM |
| 0 | mock | 30 | 38 | 55 | 57 | 72 | 74 | 76 |
| 1 | 3 | 28 | 40 | 51 | 59 | 67 | 70 | 75 |
| 2 | 4 | 30 | 47 | 59 | 65 | 75 | 82 | 82 |
| 4 | 8 | 44 | 56 | 69 | 72 | 78.5 | 82.3 | 83 |
| 8 | 14 | 47 | 60 | 70 | 78 | 80 | 84.4 | 86 |
| 16 | 40 | 70 | 79 | 83 | 84 | 86 | 89 | 89.6 |
| 32 | 89 | 86 | 89 | 88 | 89 | 87.5 | 90 | 90 |
| 64 | 93 | 94 | 94 | 95 | 95 | 95 | 95 | 95 |

TABLE 8

CI values

| sorf, μM | miR-34-Mim | | | | | | | |
|---|---|---|---|---|---|---|---|---|
| | 0 | 0.44 nM | 0.875 nM | 1.75 nM | 3.5 nM | 7 nM | 14 nM | 28 nM |
| 0 | | | | | | | | |
| 1 | | 1.26 | 0.99 | 1.23 | 1.13 | 0.98 | 1.46 | 1.76 |
| 2 | | 1.2 | 0.7 | 0.88 | 0.79 | 0.5 | 0.43 | 0.81 |
| 4 | | 0.66 | 0.53 | 0.6 | 0.54 | 0.41 | 0.47 | 0.76 |
| 8 | | 0.87 | 0.65 | 0.73 | 0.48 | 0.47 | 0.46 | 0.59 |
| 16 | | 0.7 | 0.52 | 0.56 | 0.51 | 0.45 | 0.42 | 0.5 |
| 32 | | 0.71 | 0.6 | 0.72 | 0.65 | 0.73 | 0.65 | 0.75 |
| 64 | | 0.78 | 0.78 | 0.71 | 0.7 | 0.7 | 0.71 | 0.73 |

TABLE 9

Sorafenib DRI

| sorf, μM | miR-34-Mim | | | | | | | |
|---|---|---|---|---|---|---|---|---|
| | 0 | 0.44 nM | 0.875 nM | 1.75 nM | 3.5 nM | 7 nM | 14 nM | 28 nM |
| 0 | | | | | | | | |
| 1 | | 8 | 11.2 | 14.9 | 18.3 | 22.7 | 24.8 | 29 |
| 2 | | 4.3 | 6.7 | 9.1 | 10.7 | 14.5 | 18.9 | 18.9 |
| 4 | | 3.1 | 4.2 | 6 | 6.7 | 8.2 | 9.6 | 9.9 |
| 8 | | 1.7 | 2.3 | 3.1 | 4 | 4.4 | 5.3 | 5.7 |
| 16 | | 1.6 | 2.1 | 2.5 | 2.6 | 2.9 | 3.4 | 3.5 |
| 32 | | 1.4 | 1.7 | 1.6 | 1.7 | 1.6 | 1.8 | 1.8 |
| 64 | | 1.3 | 1.3 | 1.6 | 1.6 | 1.5 | 1.6 | 1.5 |

TABLE 10 miR-34-Mim DRI

| sorf, µM | miR-34-Mim | | | | | | |
|---|---|---|---|---|---|---|---|
| | 0 | 0.44 nM | 0.875 nM | 1.75 nM | 3.5 nM | 7 nM | 14 nM | 28 nM |
| 0 | | | | | | | | |
| 1 | | 0.9 | 1.1 | 0.9 | 0.9 | 1.1 | 0.7 | 0.6 |
| 2 | | 1 | 1.8 | 1.3 | 1.4 | 2.3 | 2.6 | 1.3 |
| 4 | | 2.9 | 3.6 | 2.3 | 2.6 | 3.4 | 2.8 | 1.5 |
| 8 | | 3.6 | 4.4 | 2.4 | 4.2 | 4.1 | 3.7 | 2.4 |
| 16 | | 18.8 | 21.3 | 6.3 | 8.1 | 9.5 | 8.2 | 4.6 |
| 32 | | 97.9 | 78.8 | 10.6 | 16.8 | 12.3 | 10.0 | 5.1 |
| 64 | | 484 | 243 | 36.2 | 70.3 | 88.7 | 44.3 | 22.2 |

Conclusions:

Synergy is not a common property of anti-tumor microRNAs in combination with sorafenib. While miR-34-Mim and miR-215-Mim showed synergistic effects in combination with sorafenib, none of miR-124a-Mim, miR-101-Mim, or miR-26a-Mim showed any such effects. Moreover, synergy was not identified in combinations with two other chemotherapeutic agents—doxorubicin and 5-FU (data not shown). Synergy of certain sorafenib:miR-34-Mim combinations was consistent across all four liver cancer cell lines. Synergy of certain sorafenib:miR-34-Mim/miR-215-Mim combinations was observed at high levels of cancer cell inhibition. Synergistic sorafenib:miR-34-Mim/miR-215-Mim combinations were observed a number of ratios of miRNA mimic and sorafenib, which can be applied to developing liver cancer therapies.

Example 2

Figure 4:
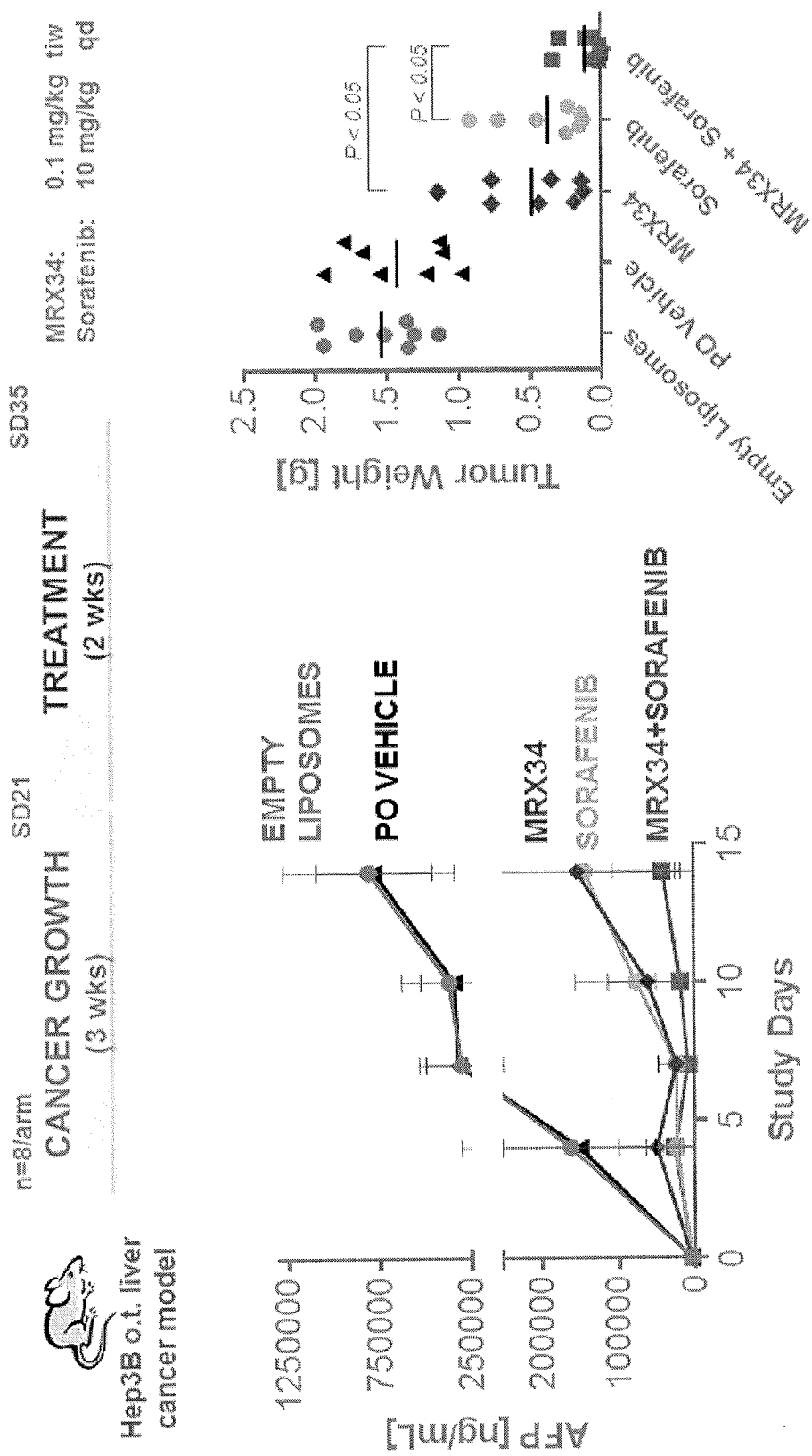
FIG. 4, which illustrates the in vivo efficacy of the miR-34-Mim/sorafenib combination in orthotopic human Hep3b xenografts.

Superior Effects of miR-34-Mim in Combination with Sorafenib in a Mouse Model of Liver Cancer Female Nod/Scid mice were orthotopically implanted with $2 \times 10^6$ Hep3b cells into the left lateral lobe of the liver. To monitor tumor growth, serum samples were collected twice a week to determine levels of alpha-fetoprotein (AFP) using DRG Human AFP ELISA, a biomarker for liver cancer. Three weeks later, mice were randomly divided into 5 groups, such that the average AFP concentration is the same in each group (n=8). Animals were treated with the single agents alone at dose levels and intervals as follows: miR-34-Mim was given intravenously three times a week at 0.1 mg/kg per administration; sorafenib was given daily by oral gavage at 10 mg/kg (M-F). For the combination, both drugs were given at the same dose and rate as each of the single agents. Control mice were treated with either (i) unloaded liposomes (NOV340, empty liposomes) by IV injection (3×/week) using a lipid concentration equivalent to 0.1 mg/kg miR-34-Mim; or (ii) PO vehicle (12.5% EtOH: 12.5% Cremaphor: 75% H2O), daily (M-F). Two weeks post treatment, serum AFP concentrations were measured for tumor growth, and tumor weights following sacrifice were collected to assess tumor regression. The data were analyzed for statistical changes using Student's t-test and/or one-way Anova with a Dunnett's Post-test (MS-Excel and Graphad Prism). The results are presented in FIG. 4, which illustrates the in vivo efficacy of the miR-34-Mim/sorafenib combination in orthotopic human Hep3b xenografts.

Example 3

Selection of Sorafenib:Oligonucleotide Ratios and Dosing

Figure 5:
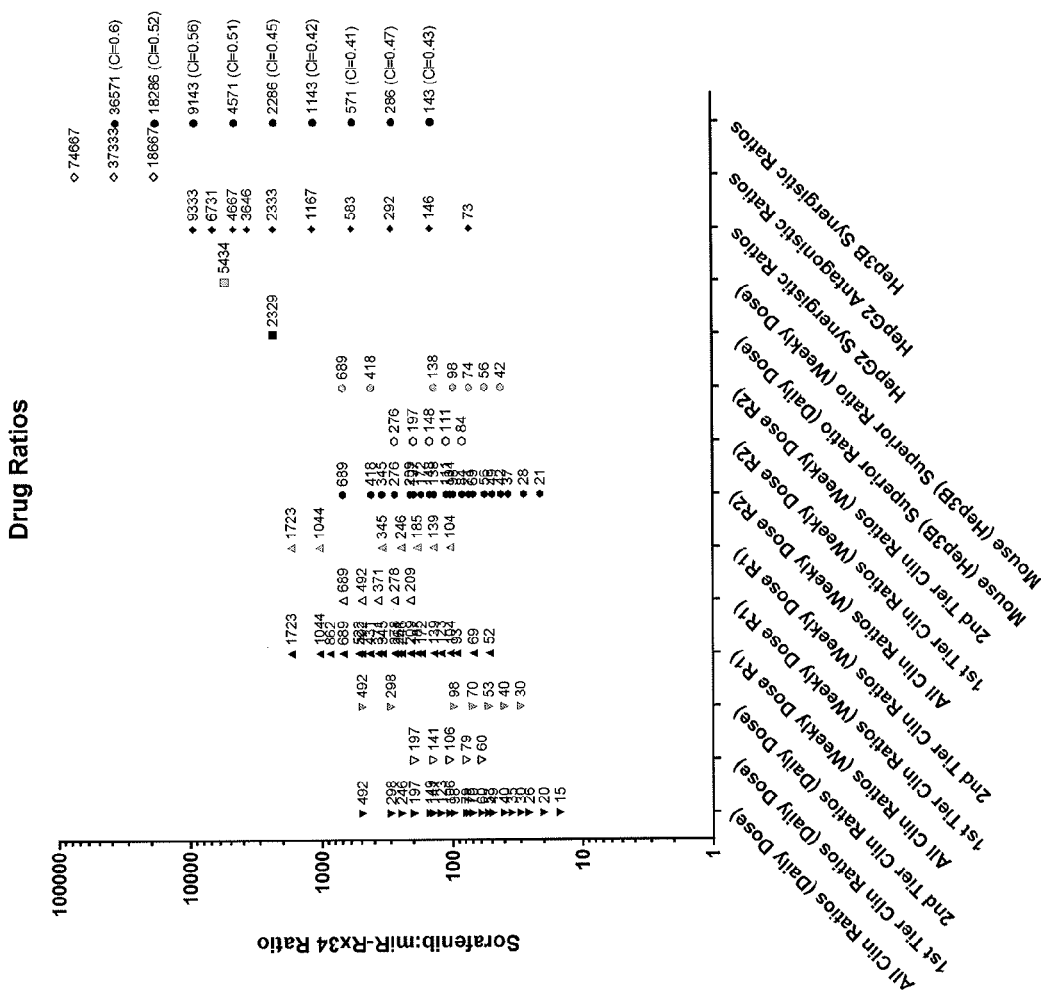
FIG. 5 presents various ranges of Sorafenib:miR-34 ratios and dosing.

FIG. 5 presents various ranges of Sorafenib:miR-34-Mim ratios and dosing. $1^{st}$ tier cohorts represent 800 mg/day sorafenib dosing and $2^{nd}$ tier cohorts represent 400 mg/day sorafenib dosing. All clinical ratios includes $1^{st}$ and $2^{nd}$ tier cohorts, as well as 200 mg/day sorafenib dosing. Weekly dose R1 indicates miR-34 administration two days per week and weekly dose R1 indicates miR-34 administration five consecutive days per week. Daily dose indicates ratios calculated over a single day's dosing, whereas weekly dose indicates ratios calculated over a single week's dosing. Other dosing schedules are possible (e.g., once per week). Oligonucleotide (in liposomal formulation) dosing can range from 50-250 mg/m².

Accordingly, in various embodiments, molar ratios can be about 15-1723, 15-492, 60-197, 30-492, 30, 40, 53, 60, 70, 79, 98, 106, 141, 197, 298, or 492. Due to synergistically increased efficacy, miR-34 doses can be lowered (e.g., lower than in miR-34 monotherapy) to achieve a desired ratio while maintaining pre-approved doses of sorafenib (e.g., FDA approved doses for monotherapy). Due to synergistically increased efficacy, in some embodiments, sorafenib doses can be lowered (e.g., below certain FDA approved doses monotherapy doses of 800 mg/day or 400 mg/day) to achieve a desired efficacy with decreased toxicity (e.g., sorafenib toxicity). In various embodiments, such combinations can provide improvements in efficacy over sorafenib monotherapy.

Ratios and dosing for miR-215, as well as all oligonucleotides in accordance with the present invention can be determined on the same basis.

It should be noted that not all ratios provide a therapeutically effective regimen. For example, synergy is not present at low doses. And, even in lower doses that could technically be considered synergistic may still not provide an effective therapy. Similarly, ratios above a certain point can prove antagonistic. See, for example, the "HepG2 Synergistic Ratios" and "HepG2 Antagonistic Ratios" ratios in FIG. 5. Therefore, in various embodiments, the invention is based not just upon data that sorafenib and miR-34 synergize in liver cancer therapy (e.g., miR-34a and HCC), but that the synergy only exists within a certain therapeutically effective range. Similar results were observed for miR-215.

Example 4

Example Sorafenib:Oligonucleotide Dosing Ranges

Tables 11-13 below present example sorafenib:oligonucleotide dosing ratios which can be clinically relevant (e.g., in human liver cancer therapy). The ratios in this example are based on moiety (not mass). The oligonucleotide can be any of the oligonucleotides in accordance with the present invention (e.g., miR-34-Mim, miR-215-Mim, and the like).

TABLE 11 example dosing ranges studied in vitro. Doses range from 1:143 (lowest) to 1:9143 (highest). The miR-Mim can be oligonucleotide in accordance with the present invention (e.g., miR-34-Mim, miR-215-Mim, and the like).

| Cultured Cells | low [nM] | high [nM] |
|---|---|---|
| Sorafenib dose range | 2000 | 16000 |
| miR-Mim dose range | 1.75 | 14 |

TABLE 11-continued example dosing ranges studied in vitro. Doses range from 1:143 (lowest) to 1:9143 (highest). The miR-Mim can be oligonucleotide in accordance with the present invention (e.g., miR-34-Mim, miR-215-Mim, and the like).

| Range | actual mg/kg | dose mg | dose/day | dose/week | nM | mol/week | ratio per day | ratio per wk |
|---|---|---|---|---|---|---|---|---|
| Sorafenib | | | | | 2000 | | | 1143 |
| miR-Mim | | | | | 1.75 | | | |
| Sorafenib | | | | | 2000 | | | 143 |
| miR-Mim | | | | | 14 | | | |
| Sorafenib | | | | | 16000 | | | 9143 |
| miR-Mim | | | | | 1.75 | | | |
| Sorafenib | | | | | 16000 | | | 1143 |
| miR-Mim | | | | | 14 | | | |

TABLE 12 example dosing ranges studied in an animal (mouse) model of human liver cancer. Doses range from 1:2 (lowest) to 1:217338 (highest), and include 1:2329 (actual). miR-Mim dosages were based on a mouse weight of 20 g. The miR-Mim can be oligonucleotide in accordance with the present invention (e.g., miR-34-Mim, miR-215-Mim, and the like).

| Actual | mg/kg | dose (mg) | dose/day | dose/week | mmol/day | mmol/week | ratio/day | ratio/week |
|---|---|---|---|---|---|---|---|---|
| Mouse | | | | | | | | |
| Sorafenib | 10 | 0.2 | 0.2 | 1.4 | 0.000314 | 0.00220 | 2329 | 5433 |
| miR-Mim | 0.1 | 0.002 | 0.002 | 0.006 | 1.35E−07 | 4.04E−07 | | |
| Practical | | | | | | | | |
| Sorafenib | 30 | 0.6 | 0.6 | 4.2 | 0.000942 | 0.00659 | 70 | 163 |
| miR-Mim | 10 | 0.2 | 0.2 | 0.6 | 1.35E−05 | 4.045E−05 | | |
| Sorafenib | 30 | 0.6 | 0.6 | 4.2 | 0.000942 | 0.00659 | 6986 | 16300 |
| miR-Mim | 0.1 | 0.002 | 0.002 | 0.006 | 1.35E−07 | 4.045E−07 | | |
| Range | | | | | | | | |
| Sorafenib | 120 | 2.4 | 2.4 | 16.8 | 0.00377 | 0.0264 | 93145 | 217338 |
| miR-Mim | 0.03 | 0.0006 | 0.0006 | 0.0018 | 4.04E−08 | 1.21E−07 | | |
| Sorafenib | 120 | 2.4 | 2.4 | 16.8 | 0.00377 | 0.0264 | 279 | 652 |
| miR-Mim | 10 | 0.2 | 0.2 | 0.6 | 1.35E−05 | 4.04E−05 | | |
| Sorafenib | 1 | 0.02 | 0.02 | 0.14 | 3.14E−05 | 0.000220 | 2 | 5 |
| miR-Mim | 10 | 0.2 | 0.2 | 0.6 | 1.35E−05 | 4.04E−05 | | |
| Sorafenib | 1 | 0.02 | 0.02 | 0.14 | 3.14E−05 | 0.000220 | 2329 | 5433 |
| miR-Mim | 0.01 | 0.0002 | 0.0002 | 0.0006 | 1.35E−08 | 4.04E−08 | | |

TABLE 13 example dosing ranges for a human subject. Doses range from 1:22 (lowest) to 1:3105 (highest). miR-Mim dosages were based on a human weight of 70 kg. The miR-Mim can be oligonucleotide in accordance with the present invention (e.g., miR-34-Mim, miR-215-Mim, and the like).

| Human | mg/kg | dose (mg) | dose/day (mg) | dose/week (mg) | mmol/day | mmol/week | ratio/day | ratio/week |
|---|---|---|---|---|---|---|---|---|
| Sorafenib | 11.4 | 800 | 800 | 5600 | 1.26 | 8.79 | 887 | 3105 |
| miR-Mim | 0.3 | 21 | 21 | 42 | 0.00142 | 0.00283 | | |
| Sorafenib | 11.4 | 800 | 800 | 5600 | 1.26 | 8.79 | 444 | 1552 |
| miR-Mim | 0.6 | 42 | 42 | 84 | 0.00283 | 0.00566 | | |
| Sorafenib | 11.4 | 800 | 800 | 5600 | 1.26 | 8.79 | 355 | 1242 |
| miR-Mim | 0.75 | 52.5 | 52.5 | 105 | 0.00354 | 0.00708 | | |
| Sorafenib | 11.4 | 800 | 800 | 5600 | 1.26 | 8.79 | 266 | 931 |
| miR-Mim | 1 | 70 | 70 | 140 | 0.00472 | 0.00944 | | |
| Sorafenib | 11.4 | 800 | 800 | 5600 | 1.26 | 8.79 | 89 | 310 |
| miR-Mim | 3 | 210 | 210 | 420 | 0.0142 | 0.0283 | | |

TABLE 13-continued example dosing ranges for a human subject. Doses range from 1:22 (lowest) to 1:3105 (highest). miR-Mim dosages were based on a human weight of 70 kg. The miR-Mim can be oligonucleotide in accordance with the present invention (e.g., miR-34-Mim, miR-215-Mim, and the like).

| Human | mg/kg | dose (mg) | dose/day (mg) | dose/week (mg) | mmol/day | mmol/week | ratio/day | ratio/week |
|---|---|---|---|---|---|---|---|---|
| Sorafenib | 5.71 | 400 | 400 | 2800 | 0.628 | 4.40 | 444 | 1552 |
| miR-Mim | 0.3 | 21 | 21 | 42 | 0.00142 | 0.00283 | | |
| Sorafenib | 5.71 | 400 | 400 | 2800 | 0.628 | 4.40 | 222 | 776 |
| miR-Mim | 0.6 | 42 | 42 | 84 | 0.00283 | 0.00566 | | |
| Sorafenib | 5.71 | 400 | 400 | 2800 | 0.628 | 4.40 | 177 | 621 |
| miR-Mim | 0.75 | 52.5 | 52.5 | 105 | 0.00354 | 0.00708 | | |
| Sorafenib | 5.71 | 400 | 400 | 2800 | 0.628 | 4.40 | 133 | 466 |
| miR-Mim | 1 | 70 | 70 | 140 | 0.00472 | 0.00944 | | |
| Sorafenib | 5.714 | 400 | 400 | 2800 | 0.628 | 4.40 | 44 | 155 |
| miR-Mim | 3 | 210 | 210 | 420 | 0.0142 | 0.0283 | | |
| Sorafenib | 2.86 | 200 | 200 | 1400 | 0.314 | 2.20 | 222 | 776 |
| miR-Mim | 0.3 | 21 | 21 | 42 | 0.00142 | 0.00283 | | |
| Sorafenib | 2.86 | 200 | 200 | 1400 | 0.314 | 2.20 | 111 | 388 |
| miR-Mim | 0.6 | 42 | 42 | 84 | 0.00283 | 0.00566 | | |
| Sorafenib | 2.86 | 200 | 200 | 1400 | 0.314 | 2.20 | 89 | 310 |
| miR-Mim | 0.75 | 52.5 | 52.5 | 105 | 0.00354 | 0.00708 | | |
| Sorafenib | 2.86 | 200 | 200 | 1400 | 0.314 | 2.20 | 67 | 233 |
| miR-Mim | 1 | 70 | 70 | 140 | 0.00472 | 0.00944 | | |
| Sorafenib | 2.86 | 200 | 200 | 1400 | 0.314 | 2.20 | 22 | 78 |
| miR-Mim | 3 | 210 | 210 | 420 | 0.0142 | 0.0283 | | |

TABLE 14 example human clinical dosing ranges based on a 70 kg patient (sorafenib mw = 637, miR-34 mw = 14834), based upon daily dosing of sorafenib and miR-Mim. The miR-Mim can be oligonucleotide in accordance with the present invention (e.g., miR-34-Mim, miR-215-Mim, and the like).

| | mg | | | molar | | |
|---|---|---|---|---|---|---|
| Ratio | sorafenib [mg] | miR-Mim [mg] | miR-Mim [mg/m²] | miR-Mim | sorafenib [mmol] | miR-Mim [mmol] |
| 5286 | 200 | 38 | 20 | 123 | 0.3140 | 0.0026 |
| 3203 | 200 | 62 | 33 | 75 | 0.3140 | 0.0042 |
| 2114 | 200 | 95 | 50 | 49 | 0.3140 | 0.0064 |
| 1510 | 200 | 132 | 70 | 35 | 0.3140 | 0.0089 |
| 1137 | 200 | 176 | 93 | 26 | 0.3140 | 0.0119 |
| 853 | 200 | 235 | 124 | 20 | 0.3140 | 0.0158 |
| 641 | 200 | 312 | 165 | 15 | 0.3140 | 0.0210 |
| 10571 | 400 | 38 | 20 | 246 | 0.6279 | 0.0026 |
| 6407 | 400 | 62 | 33 | 149 | 0.6279 | 0.0042 |
| 4229 | 400 | 95 | 50 | 98 | 0.6279 | 0.0064 |
| 3020 | 400 | 132 | 70 | 70 | 0.6279 | 0.0089 |
| 2273 | 400 | 176 | 93 | 53 | 0.6279 | 0.0119 |
| 1705 | 400 | 235 | 124 | 40 | 0.6279 | 0.0158 |
| 1281 | 400 | 312 | 165 | 30 | 0.6279 | 0.0210 |
| 21143 | 800 | 38 | 20 | 492 | 1.2559 | 0.0026 |
| 12814 | 800 | 62 | 33 | 298 | 1.2559 | 0.0042 |
| 8457 | 800 | 95 | 50 | 197 | 1.2559 | 0.0064 |
| 6041 | 800 | 132 | 70 | 141 | 1.2559 | 0.0089 |
| 4547 | 800 | 176 | 93 | 106 | 1.2559 | 0.0119 |
| 3410 | 800 | 235 | 124 | 79 | 1.2559 | 0.0158 |
| 2563 | 800 | 312 | 165 | 60 | 1.2559 | 0.0210 |

TABLE 15 example human clinical dosing ranges based on a 70 kg patient (sorafenib mw = 637, miR-34 mw = 14834), based upon daily dosing of sorafenib and biweekly dosing of miR-Mim. The miR-Mim can be oligonucleotide in accordance with the present invention (e.g., miR-34-Mim, miR-215-Mim, and the like).

| | Daily Dose | | | | | | Weekly Dose | | |
|---|---|---|---|---|---|---|---|---|---|
| | mg | | | | molar | | All Ratios | | |
| Ratio | Soraf. [mg] | miR-Mim [mg] | miR-Mim [mg/m²] | Ratio | Soraf. [mmol] | miR-Mim [mmol] | Ratio | Soraf. [mmol] | miR-Mim [mmol] |
| 5286 | 200 | 38 | 20 | 123 | 0.3140 | 0.0026 | 431 | 2.1978 | 0.0051 |
| 3203 | 200 | 62 | 33 | 75 | 0.3140 | 0.0042 | 261 | 2.1978 | 0.0084 |
| 2114 | 200 | 95 | 50 | 49 | 0.3140 | 0.0064 | 172 | 2.1978 | 0.0127 |
| 1510 | 200 | 132 | 70 | 35 | 0.3140 | 0.0089 | 123 | 2.1978 | 0.0178 |
| 1137 | 200 | 176 | 93 | 26 | 0.3140 | 0.0119 | 93 | 2.1978 | 0.0237 |
| 853 | 200 | 235 | 124 | 20 | 0.3140 | 0.0158 | 69 | 2.1978 | 0.0316 |
| 641 | 200 | 312 | 165 | 15 | 0.3140 | 0.0210 | 52 | 2.1978 | 0.0420 |
| 10571 | 400 | 38 | 20 | 246 | 0.6279 | 0.0026 | 862 | 4.3956 | 0.0051 |

TABLE 15-continued

| | Daily Dose | | | | | | Weekly Dose | |
| | mg | | | molar | | | All Ratios | |
| Ratio | Soraf. [mg] | miR-Mim [mg] | miR-Mim [mg/m$^2$] | Ratio | Soraf. [mmol] | miR-Mim [mmol] | Ratio | Soraf. [mmol] | miR-Mim [mmol] |
|---|---|---|---|---|---|---|---|---|---|
| 6407 | 400 | 62 | 33 | 149 | 0.6279 | 0.0042 | 522 | 4.3956 | 0.0084 |
| 4229 | 400 | 95 | 50 | 98 | 0.6279 | 0.0064 | 345 | 4.3956 | 0.0127 |
| 3020 | 400 | 132 | 70 | 70 | 0.6279 | 0.0089 | 246 | 4.3956 | 0.0178 |
| 2273 | 400 | 176 | 93 | 53 | 0.6279 | 0.0119 | 185 | 4.3956 | 0.0237 |
| 1705 | 400 | 235 | 124 | 40 | 0.6279 | 0.0158 | 139 | 4.3956 | 0.0316 |
| 1281 | 400 | 312 | 165 | 30 | 0.6279 | 0.0210 | 104 | 4.3956 | 0.0420 |
| 21143 | 800 | 38 | 20 | 492 | 1.2559 | 0.0026 | 1723 | 8.7912 | 0.0051 |
| 12814 | 800 | 62 | 33 | 298 | 1.2559 | 0.0042 | 1044 | 8.7912 | 0.0084 |
| 8457 | 800 | 95 | 50 | 197 | 1.2559 | 0.0064 | 689 | 8.7912 | 0.0127 |
| 6041 | 800 | 132 | 70 | 141 | 1.2559 | 0.0089 | 492 | 8.7912 | 0.0178 |
| 4547 | 800 | 176 | 93 | 106 | 1.2559 | 0.0119 | 371 | 8.7912 | 0.0237 |
| 3410 | 800 | 235 | 124 | 79 | 1.2559 | 0.0158 | 278 | 8.7912 | 0.0316 |
| 2563 | 800 | 312 | 165 | 60 | 1.2559 | 0.0210 | 209 | 8.7912 | 0.0420 | example human clinical dosing ranges based on a 70 kg patient (sorafenib mw = 637, miR-34 mw = 14834), based upon daily dosing of sorafenib and five daily doses of miR-Mim per week. The miR-Mim can be oligonucleotide in accordance with the present invention (e.g., miR-34-Mim, miR-215-Mim, and the like).

| Ratio | Soraf. [mg] | miR-Mim [mg] | miR-Mim [mg/m$^2$] | Ratio | Soraf. [mmol] | miR-Mim [mmol] | Ratio | Soraf. [mmol] | miR-Mim [mmol] |
|---|---|---|---|---|---|---|---|---|---|
| 5286 | 200 | 38 | 20 | 123 | 0.3140 | 0.0026 | 172 | 2.1978 | 0.0127 |
| 3203 | 200 | 62 | 33 | 75 | 0.3140 | 0.0042 | 104 | 2.1978 | 0.0210 |
| 2114 | 200 | 95 | 50 | 49 | 0.3140 | 0.0064 | 69 | 2.1978 | 0.0318 |
| 1510 | 200 | 132 | 70 | 35 | 0.3140 | 0.0089 | 49 | 2.1978 | 0.0446 |
| 1137 | 200 | 176 | 93 | 26 | 0.3140 | 0.0119 | 37 | 2.1978 | 0.0593 |
| 853 | 200 | 235 | 124 | 20 | 0.3140 | 0.0158 | 28 | 2.1978 | 0.0790 |
| 641 | 200 | 312 | 165 | 15 | 0.3140 | 0.0210 | 21 | 2.1978 | 0.1052 |
| 10571 | 400 | 38 | 20 | 246 | 0.6279 | 0.0026 | 345 | 4.3956 | 0.0127 |
| 6407 | 400 | 62 | 33 | 149 | 0.6279 | 0.0042 | 209 | 4.3956 | 0.0210 |
| 4229 | 400 | 95 | 50 | 98 | 0.6279 | 0.0064 | 138 | 4.3956 | 0.0318 |
| 3020 | 400 | 132 | 70 | 70 | 0.6279 | 0.0089 | 98 | 4.3956 | 0.0446 |
| 2273 | 400 | 176 | 93 | 53 | 0.6279 | 0.0119 | 74 | 4.3956 | 0.0593 |
| 1705 | 400 | 235 | 124 | 40 | 0.6279 | 0.0158 | 56 | 4.3956 | 0.0790 |
| 1281 | 400 | 312 | 165 | 30 | 0.6279 | 0.0210 | 42 | 4.3956 | 0.1052 |
| 21143 | 800 | 38 | 20 | 492 | 1.2559 | 0.0026 | 689 | 8.7912 | 0.0127 |
| 12814 | 800 | 62 | 33 | 298 | 1.2559 | 0.0042 | 418 | 8.7912 | 0.0210 |
| 8457 | 800 | 95 | 50 | 197 | 1.2559 | 0.0064 | 276 | 8.7912 | 0.0318 |
| 6041 | 800 | 132 | 70 | 141 | 1.2559 | 0.0089 | 197 | 8.7912 | 0.0446 |
| 4547 | 800 | 176 | 93 | 106 | 1.2559 | 0.0119 | 148 | 8.7912 | 0.0593 |
| 3410 | 800 | 235 | 124 | 79 | 1.2559 | 0.0158 | 111 | 8.7912 | 0.0790 |
| 2563 | 800 | 312 | 165 | 60 | 1.2559 | 0.0210 | 84 | 8.7912 | 0.1052 |

In some embodiments where a human subject is treated, the sorafenib dose is 800 mg/day and miR-Mim (e.g., miR-34-Mim in liposomal formulation) is 1 mg/kg/day, which results in a ratio of 1:266 and 1:931 on a daily and weekly basis, respectively.

In other embodiments where a human subject is treated, both the sorafenib and miR-Mim are administered at the maximum tolerated dose (MTD). Assuming a MTD of 3 mg/kg for miR-34 (in liposomal formulation), the doses would be in a ratio of 1:89 and 1:310 on a daily and weekly basis, respectively. Such doses are in agreement with the synergistic ratios identified through the in vitro studies discussed in the examples above. In various embodiments, the desired ratio can be achieved by reducing the dose of miR-Mim relative to sorafenib.

Example 5

Combination Therapies Based Upon 800 mg/Day Sorafenib

For clinical practice, the miR-34-Mim+sorafenib combination is used as follows. Patient is given a daily oral dose of 800 mg sorafenib (400 mg twice per day) and an intravenous 30 min to 3 hr infusion of miR-34-Mim at dose levels ranging from 50 mg/m$^2$ to 165 mg/m$^2$. These dose levels represent 60 to 197 molar ratios of sorafenib vs. miR-34 mimic per day based on a 70 kg patient. In particular situations, miR-34-Mim is given at dose levels of 50, 70, 93, 124 or 165 mg/m$^2$. These dose levels represent molar ratios of 197, 141, 106, 79 and 60 between sorafenib and miR-34 mimic per day based on a 70 kg patient.

In another example sorafenib is given as a daily oral dose of 800 mg and miR-34-Mim is given three twice a week (for instance Mondays and Thursdays) during a 30 min to 3 hr infusion at dose levels ranging from 50 mg/m$^2$ to 165 mg/m$^2$. These dose levels represent 209 to 689 molar ratios of sorafenib vs. miR-34 mimic per week based on a 70 kg patient. In particular situations, miR-34-Mim is given at dose levels of 50, 70, 93, 124 or 165 mg/m$^2$. These dose levels represent molar ratios of 689, 492, 371, 278 and 209 between sorafenib and miR-34 mimic per week based on a 70 kg patient.

In another example, sorafenib is given as a daily oral dose of 800 mg and miR-34-Mim is given daily by an intravenous 30 min to 3 hr infusion at dose levels ranging from 50 mg/m$^2$ to 165 mg/m$^2$ on five consecutive days with the following two days off per week. These dose levels represent 84 to 276 molar ratios of sorafenib vs. miR-34 mimic per week based on a 70 kg patient. In particular situations, miR-34-Mim is given at dose levels of 50, 70, 93, 124 or 165 mg/m$^2$. These dose levels represent molar ratios of 276, 197, 148, 111 and 84 between sorafenib and miR-34 mimic per week based on a 70 kg patient.

Ratios and dosing for miR-215, as well as all oligonucleotides in accordance with the present invention can be determined on the same basis.

Example 6

Combination Therapies Based Upon 400 mg/Day Sorafenib

In another example, the miR-34-Mim+sorafenib combination is used as follows. Patient is given a daily oral dose of 400 mg sorafenib and an intravenous 30 min to 3 hr infusion of miR-34-Mim at dose levels ranging from 50 mg/m$^2$ to 165 mg/m$^2$. These dose levels represent 30 to 98 molar ratios of sorafenib vs. miR-34 mimic per day based on a 70 kg patient. In particular situations, miR-34-Mim is given at dose levels of 50, 70, 93, 124 or 165 mg/m$^2$. These dose levels represent molar ratios of 98, 70, 53, 40 and 30 between sorafenib and miR-34 mimic per day based on a 70 kg patient.

In another example sorafenib is given as a daily oral dose of 400 mg and miR-34-Mim is given three twice a week (for instance Mondays and Thursdays) during a 30 min to 3 hr infusion at dose levels ranging from 50 mg/m$^2$ to 165 mg/m$^2$. These dose levels represent 104 to 345 molar ratios of sorafenib vs. miR-34 mimic per week based on a 70 kg patient. In particular situations, miR-34-Mim is given at dose levels of 50, 70, 93, 124 or 165 mg/m$^2$. These dose levels represent molar ratios of 345, 246, 185, 139 and 104 between sorafenib and miR-34 mimic per week based on a 70 kg patient.

In another example, sorafenib is given as a daily oral dose of 400 mg and miR-34-Mim is given daily by an intravenous 30 min to 3 hr infusion at dose levels ranging from 50 mg/m$^2$ to 165 mg/m$^2$ on five consecutive days with the following two days off per week. These dose levels represent 42 to 138 molar ratios of sorafenib vs. miR-34 mimic per week based on a 70 kg patient. In particular situations, miR-34-Mim is given at dose levels of 50, 70, 93, 124 or 165 mg/m$^2$. These dose levels represent molar ratios of 138, 98, 74, 56 and 42 between sorafenib and miR-34 mimic per week based on a 70 kg patient.

Ratios and dosing for mir-215, as well as all oligonucleotides in accordance with the present invention can be determined on the same basis.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. Those skilled in the art will recognize, or be able to ascertain using no more than routine experimentation, many equivalents to the specific embodiments of the invention described herein. Such equivalents are intended to be encompassed by the following claims.

The invention claimed is:

1. A synergistic compound combination comprising a synergistically effective amount of: (a) sorafenib; and (b) a 17-30 basepair synthetic oligonucleotide comprising:
   (i) a guide strand comprising a sequence according to SEQ ID NO:9;
   (ii) a separate passenger strand that is at least 60% complementary to the guide strand; and
   (iii) a 5' end nucleotide modification on the passenger strand, wherein the 5' end nucleotide modification is: a 5' end terminal nucleotide cap; a mismatch at the first nucleotide at the 5' end of the passenger strand; a mismatch at the second nucleotide at the 5' end of the passenger strand; or any combinations thereof.

2. The synergistic compound combination of claim 1, wherein the synthetic oligonucleotide is 20-23 basepairs in length.

3. The synergistic compound combination of claim 2, wherein the synthetic oligonucleotide comprises a sequence according to SEQ ID NO:1, SEQ ID NO:2, or SEQ ID NO:3.

4. The synergistic compound combination of claim 2, wherein the synthetic oligonucleotide comprises a sequence according to SEQ ID NO:5, SEQ ID NO:6, or SEQ ID NO:7.

5. The synergistic compound combination of claim 1, wherein the 5' end terminal nucleotide cap on the passenger strand is a C6 alkylamine group.

6. A method of treating a liver cancer in a subject in need thereof, comprising:
   administering to the subject the synergistic combination of claim 1.

7. The method of claim 6, wherein the liver cancer is primary liver cancer.

8. The method of claim 7, wherein the liver cancer is hepatocellular carcinoma (HCC).

9. The method of claim 6, wherein the synergy is quantified as (a) a level of cancer cell inhibition greater than about 70%; (b) a combination index (CI) of less than about; and (c) a dose reduction index (DRI) greater than about 2.0 for both sorafenib and the oligonucleotide.

10. The method of claim 6, wherein the molar ratio of sorafenib:oligonucleotide administered to the subject is in the range of about 15:1 to 2032:1.

11. The method of claim 6, wherein the molar ratio of sorafenib:oligonucleotide administered to the subject is in the range of about 15:1 to 1723:1.

12. The method of claim 6, wherein the molar ratio is based on the amount of sorafenib:oligonucleotide administered to the subject in a single day, a single week, 14 days, 21 days, or 28 days.

13. The method of claim 6, wherein the oligonucleotide is administered to the subject prior to the sorafenib, concurrently with the sorafenib, or after the sorafenib.

14. The method of claim 6, wherein the liver cancer has primary or secondary resistance to sorafenib.

15. A method of inhibiting proliferation of liver cancer cells, the method comprising administering the synergistic combination of claim 1.

16. A method of treating a hepatocellular carcinoma (HCC) in a subject in need thereof, comprising:
administering to the subject the synergistic combination of claim 1, wherein the synthetic oligonucleotide comprises a sequence according to SEQ ID NO:1.

17. The method of claim 16, wherein the synergy is quantified as (a) a level of cancer cell inhibition greater than about 70%; (b) a combination index (CI) of less than about 0.60; and (c) a dose reduction index (DRI) greater than about 2.0 for both sorafenib and the oligonucleotide.

18. The method of claim 16, wherein the molar ratio of sorafenib:oligonucleotide is in the range of about 15:1 to 2032:1.

19. The method of claim 16,
wherein the oligonucleotide is administered to the subject in an amount of about 10, 20, 25, 30, 40, 50, 75, 100, 125, 150, 175, 200, 225, or 250 mg/m$^2$ per day;
wherein the sorafenib is administered to the subject in an amount of about 800, 600, 400, or 200 mg/day;
wherein the molar ratio of sorafenib:oligonucleotide administered to the subject is in the range of about 15:1 to 2032:1 based on the amount of sorafenib:oligonucleotide administered to the subject in a single day, a single week, 14 days, 21 days, or 28 days.

* * * * *